(12) United States Patent
Zhou et al.

(10) Patent No.: US 9,266,911 B2
(45) Date of Patent: Feb. 23, 2016

(54) CAMPTOTHECIN DERIVATIVE, AND PREPARATION METHOD THEREOF, AND PHARMACEUTICAL COMPOSITION AND APPLICATION

(71) Applicants: Wenqiang Zhou, Changsha (CN); Jing Deng, Changsha (CN)

(72) Inventors: Wenqiang Zhou, Changsha (CN); Jing Deng, Changsha (CN)

( * ) Notice: Subject to any disclaimer, the term of this patent is extended or adjusted under 35 U.S.C. 154(b) by 0 days.

(21) Appl. No.: 14/134,346

(22) Filed: Dec. 19, 2013

(65) Prior Publication Data
US 2014/0107342 A1   Apr. 17, 2014

Related U.S. Application Data

(63) Continuation-in-part of application No. PCT/CN2012/000712, filed on May 22, 2012.

(30) Foreign Application Priority Data

Jun. 30, 2011  (CN) .......................... 2011 1 0181406

(51) Int. Cl.
*C07F 9/6533*  (2006.01)
*C07F 9/6561*  (2006.01)
(Continued)

(52) U.S. Cl.
CPC .......... *C07F 9/65335* (2013.01); *C07D 491/22* (2013.01); *C07F 7/0812* (2013.01); *C07F 7/0814* (2013.01); *C07F 9/6561* (2013.01)

(58) Field of Classification Search
CPC . C07F 9/65335; C07F 9/6561; C07D 491/22; A61K 31/675; A61P 35/00
USPC ...................... 546/23; 514/89, 283
See application file for complete search history.

(56) References Cited

U.S. PATENT DOCUMENTS 4,943,579 A * 7/1990 Vishnuvajjala et al. ...... 514/283

FOREIGN PATENT DOCUMENTS

| CN | 102153607 | * | 8/2011 |
| JP | 62195393 | * | 8/1987 |

OTHER PUBLICATIONS

Khandazhinskaya; Expert Opin. Drug Metab. Toxicol., 2010, 6, 701-714.*

(Continued)

*Primary Examiner* — Janet L Andres
*Assistant Examiner* — Daniel Carcanague
(74) *Attorney, Agent, or Firm* — Yimei C. Hammond; Kremblas & Foster

(57) ABSTRACT

The present invention relates to a camptothecin derivative having a structure as represented by Formula (II), in which $X^{n+}$ is selected from $H^+$, $K^+$, $Na^+$, $Li^+$, $Mg^{2+}$, $Ca^{2+}$, $Zn^{2+}$, $Fe^{3+}$, and ammonium ion, while $R^1$, $R^2$, $R^3$, and $R^4$ independently represent a hydrogen, a hydroxyl group, a nitro group, a cyano group, a halogen, a carboxyl group, an optionally substituted amino group, a silicon-containing group, a monocyclic aryloxy group, an optionally substituted C1-C6 alkoxy group, an optionally substituted C1-C6 alkylcarbonyl group, an optionally substituted C1-C6 alkyl group, or an optionally substituted C3-C6 cycloalkyl group; alternatively, $R^1$ and $R^2$ are connected via one to three other atoms to form a heterocyclic ring; and in another embodiment, $R^3$ and $R^4$ are oxygen atoms and connected via —O—$(CH_2)_n$—O—, forming a ring, in which n=1 or 2. The compound has great water-solubility, chemical stability, and great efficacy in treatment on cancer.

Formula (II)

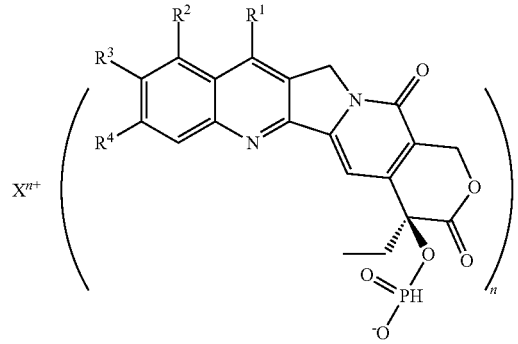

14 Claims, 9 Drawing Sheets

(51) Int. Cl.
*C07D 491/22* (2006.01)
*A61K 31/675* (2006.01)
*A61P 35/00* (2006.01)
*C07F 7/08* (2006.01)

(56) References Cited

OTHER PUBLICATIONS

Pommier, Yves; Topoisomerase I Inhibitors: Comptothecins and Beyond; Nature Reviews/Cancer; Oct. 2006; pp. 789-802; vol. 6.

Thomas, Craig J., et al.; Camptothecin: Current Perspectives; Bioorganic & Medicinal Chemistry 12; 2004; pp. 1585-1604.

Burke, Thomas G. et al.; Ethyl Substitution at the 7 Position Extends the Half-Life of 10-Hydroxycamptothecin in the Presence of Human Serum Albumin; J. Med. Chem. 1993, vol. 36; pp. 2580-2582.

Burke, Thomas G., et al.; Preferential Binding of the Carboxylate Form of Camptothecin by Human Serum Albumin; Analystical Biochemistry 212; 1993; pp. 285-287.

Mi, Zihou et al.; Differential Interactions of Camptothecin Lactone and Carboxylate Forms with Human Blood Components; Biochemistry 1994; vol. 33; pp. 10325-10336.

Burke, Thomas et al.; The Important Role of Albumin in Determining the Relative Human Blood Stabilities of the Camptothecin Anticancer Drugs; (Corrections and Additions, P1492) Journal of Pharmaceutical Sciences; vol. 84, No. 12, Dec. 1995; p. 518-519.

Verma, Rajeshwar et al.; Camptothecins: A SAR/QSAR Study; Chem. Rev. 2009; vol. 109; pp. 213-235.

Rahier, Nicolas J., et al.; Water-Soluble Camptothecin Derivatives that Are Intrinsic Topoisomerase I Poisons; Organic Letters; 2004; vol. 6, No. 3; pp. 321-324.

Wall, Monroe E., et al.; Plant antitumor agents. I. Isolation and structure of camtothecin, a novel alkaloidal leukemia and tumor inhibitor from Camptotheca acuminata; Journal of the American Chemical Society (1966), 88(16), 3888-90 CODEN: JACSAT; ISSN: 0002-7863. English.

* cited by examiner

CAMPTOTHECIN DERIVATIVE, AND PREPARATION METHOD THEREOF, AND PHARMACEUTICAL COMPOSITION AND APPLICATION

This application is a continuation-in-part of PCT Application Serial No. PCT/CN2012/000712, filed on May 22, 2012; which claims the benefits of foreign priority of Chinese Application Serial No. CN201110181406.0, filed on Jun. 30, 2011. The entire contents of PCT Application Serial No. PCT/CN2012/000712 and Chinese Application Serial No. CN201110181406.0 are incorporated by reference herein.

FIELD OF THE INVENTION

The present invention relates to the field of pharmaceutics, particularly to the field of anticancer drugs, more particularly to compounds of small molecule drugs, methods of preparation thereof and pharmaceutical applications.

BACKGROUND OF THE INVENTION

The native Camptothecin ("CPT") has a pentacyclic structure of a fused ring system consisting of quinoline rings (Ring A and Ring B), a pyrrolidine ring (Ring C), an alpha-pyridone ring (Ring D), and a six-membered lactone ring (Ring E). CPT has only one asymmetric center at 20-position and displays dextro-rotation due to the S-configuration of a tertiary hydroxyl group. CPT is a cytotoxic alkaloid which was first isolated and characterized by Wall and his coworkers (*J. Am. Chem. Soc.* 88, 3888, 1966) from leaves and barks of Camptotheca accuminata (NYSSACEAE), a plant native to China. The primary cellular target for CPT is topoisomerase I (topo I), an enzyme involved in the relaxation of supercoiled chromosomal DNA during DNA replication by transient single-strand cleavage of duplex DNA, unwinding and religation. CPT binds at the interface of covalent binary topo I-DNA complex to form stable ternary complex, which prevents the religation of DNA after the unwinding, and consequently leads to replication-mediated double-strand breaks and DNA damage. Because CPT inhibition can lead to cell death during S-phase of the cell cycle, CPT has become the focus of extensive studies in anticancer drug development (*Nature Review/Cancer*, October 2006 Vol. 6, pp 789-802; *Bioorg. Med. Chem.*, 2004, 12, pp 1585-1604).

The native CPT is not soluble in water or in other aqueous vehicles that are suitable for parental administration. At pH 7 or above, the E-ring lactone structure of CPT can be hydrolyzed to form the ring-opened carboxylate derivative, which is water-soluble but lacks of the biological activity required and exhibits high clinical toxicity. At the physiological condition, the E-ring lactone hydrolysis reaction may be exacerbated due to the preferential binding (150-fold higher than CPT) of the carboxylate derivative to human serum album (*J. Med. Chem.* 1993, 36, 2580; *Anal. Biochem.* 1993, 212, 285; *Biochemistry*, 1994, 33, 10325; *Biochemistry*, 1994, 33, 10325; *Pharm. Sci.* 1995, 84. 518). The water-insolubility of CPT and the clinical toxicity of its carboxylate derivative are two limiting factors preventing CPT from being used as an antitumor chemotherapeutic agent in clinical applications (*Nature Review/Cancer*, October 2006 Vol. 6, pp 789-802). It thus would be desirable to find CPT derivatives with better in vivo lactone stability and water-solubility than native CPT (*Bioorg. Med. Chem.*, 2004, 12, pp 1585-1604; *Chem. Rev.*, 2009, 109 (1), pp 213-235).

In literature, the attempts to develop the bioactive CPT analogs with better water solubility have been focused on introducing hydrophilic groups to the A, B, or/and C ring(s) of CPT (*Bioorg. Med. Chem.*, 2004, 12, pp 1585-1604; *Chem. Rev.*, 2009, 109 (1), pp 213-235). Compared to the native CPT, attaching chemical modifying groups to the fused ring system would, to some extent, adversely affect CPT's binding to the surface of covalent binary topo I-DNA complex to form stable tertiary complex. As a result, the bioactivity of these CPT analogs (e.g. Topotecan, which is used as a standard anticancer drug to inhibit cancer cell growth) is generally less than that of CPT (*Nature Review/Cancer*, October 2006 Vol. 6, pp 789-802; *Bioorg. Med. Chem.*, 2004, 12, pp 1585-1604). On the other hand, chemical modification at the A, B, C rings of CPT cannot mitigate the hydrolysis of the E-ring lactone. It is generally believed that the E-ring lactone hydrolysis is facilitated by the hydrogen bonding interaction between the 20(S)-hydroxyl group and the neighboring carbonyl group (*Bioorg. Med. Chem.*, 2004, 12, pp 1585-1604; *Chem. Rev.*, 2009, 109 (1), pp 213-235). Previous literature has shown that, in order to increase CPT lactone ring stability, one approach is to disrupt the hydrogen bond interaction between the 20(S)-hydroxyl and the neighboring carbonyl, e.g. by reaction of the 20(S)-hydroxyl with alkyl or acyl to form ether or ester, thereby preventing acceleration of the E-ring lactone hydrolysis. However, the 20(S)-hydroxyl group is essential for the pharmacological activity of CPT. The CPT analogs without the 20(S)-hydroxyl group generally are proven to lack of antitumor efficacy (*Organic Lett.*, 2004, 6(3), pp 321-324; *Bioorg. Med. Chem.*, 2004, 12, pp 1585-1604; *Chem. Rev.*, 2009, 109 (1), pp 213-235).

From the above discussion, the strategy to attach a water-soluble prodrug group (e.g. ionized functional group) to the 20(S)-hydroxyl site would be a practical approach to increase the water-solubility of the resulting prodrug molecule (feasibility of drug administration) while improving the E-ring lactone stability of the CPT prodrug in blood during circulation (clinical safety of the drug). By doing so, this prodrug approach would convert the water-insoluble CPT molecule to the water-soluble CPT prodrug; because such a water-soluble CPT prodrug could quickly diffuse to the whole human body after entering the blood stream, the CPT prodrug would exist in very low concentration during the metabolism, thereby preventing precipitation of CPT in the blood vessels. In addition, by introducing a screening prodrug group at the 20(S)-hydroxyl site, the hydrogen bond interaction between the 20(S)-hydroxyl and the neighboring carbonyl, which would facilitate the E-ring lactone hydrolysis, could be prevented. As a result, the E-ring lactone stability of the CPT prodrug in blood stream during circulation could be enhanced, and the clinical drug safety concerns, e.g. hematotoxicity related to carboxylate derivative generated by CPT hydrolysis, could be mitigated. Obviously, the prodrug approach of protecting the 20(S) hydroxyl site with a water-soluble prodrug group is a medicinal chemistry method which can bring in lactone stability, water-solubility and bioactivity to facilitate CPT anti-cancer drug development.

The attempts to prepare the CPT prodrugs or CPT-based compounds by chemical modification of the 20(S)-hydroxyl site have been reported in literature. Among them, most efforts were to introduce various protecting functional groups (including lipophilic and charged functional groups) through esterification of the 20(S)-hydroxyl group (*Chem. Rev.*, 2009, 109 (1), pp 213-235). Conversion of the ester prodrug to the native CPT is mediated by a group of enzymes known as esterases, which exist widely in the blood of animals (including humans). The shortcoming of the ester prodrugs is the relatively poor stability of the ester linkage in human body at physiological condition, which is easy to break by esterases. The clinical benefit of the CPT ester prodrug approach was not promising (*Chem. Rev.*, 2009, 109 (1), pp 213-235). In another attempt, the CPT 20(S)—O-phosphonate esters have been prepared (*Organic Lett.*, 2004, 6(3), pp 321-324). The disclosed 20(S)—O-phosphonates could improve water-solubility and in vivo lactone stability of CPT, but as tested in experiments, the CPT derivatives of 20(S)—O-phosphonates lack of antitumor activities (*Organic Lett.*, 2004, 6(3), pp 321-324). The 20(S)—O-phosphonate esters cannot be converted to CPT at the physiological conditions (*Organic Lett.*, 2004, 6(3), pp 321-324).

It thus would be still desirable to develop CPT derivatives which have acceptable water-soluble and E-ring lactone stability, as well as good anticancer efficacy.

SUMMARY OF THE INVENTION

One object of the present invention is to provide a novel campthothcin derivative with ideal antitumor efficacy, water-solubility, and E-ring lactone stability.

Another object of the present invention is to provide a method to prepare the above-mentioned CPT derivative.

One further object of the present invention is to provide uses of the above-mentioned CPT derivative in preparing a pharmaceutical for treating cancer.

In one aspect of the present invention, a CPT-phosphite of Formula I is provided,

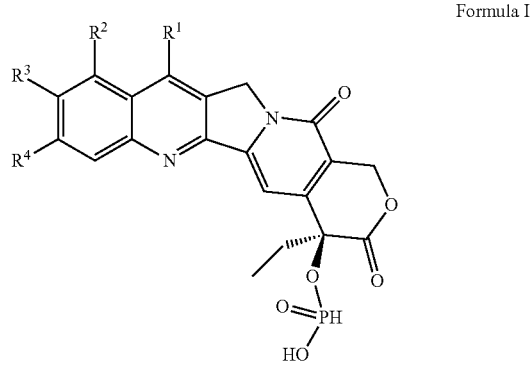

Formula I wherein $R^1$, $R^2$, $R^3$, and $R^4$ independently represent hydrogen, hydroxy, nitro, cyano, halo, carboxy, optionally substituted amino, a silicon-containing group (e.g. silyl, siloxyl, for example, containing C1-C6, but the present invention is not limited thereto), mono-ring aryloxy, C1-C6 alkoxy optionally substituted by hydroxy, nitro, cyano, halo or amino, C1-C6 alkanoyl optionally substituted by hydroxy, nitro, cyano, halo or amino, C1-C6 alkyl optionally substituted by hydroxy, nitro, cyano, halo or amino, or C3-C6 cycloalkyl optionally substituted by hydroxy, nitro, cyano, halo or amino; or $R^1$ and $R^2$ are connected via one to three other atoms to form a heterocycle, wherein the heterocycle is an N-heterocycle, S-heterocycle, O-heterocycle, or a heterocycle containing two heteroatoms which are selected from the group consisting of N, O and S, and $R^3$ and $R^4$ are defined as above; or R1 and R2 are defined as above, and R3, R4 are oxygen atoms and connected via —O—(CH$_2$)$_n$—O— to form a ring compound, wherein n is 1 or 2.

In a second aspect of the present invention, a CPT phosphite salt of Formula II is provided,

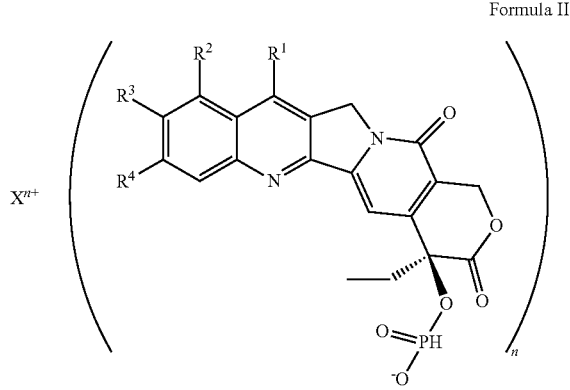

Formula II wherein $R^1$, $R^2$, $R^3$, $R^4$ are defined as above, and $X^{n+}$ is selected from $K^+$, $Na^+$, $Li^+$, $Mg^{2+}$, $Ca^{2+}$, $Zn^{2+}$, $Fe^{3+}$, and ammonium.

The present invention also relates to preparation of the above-described compounds, and pharmaceutical compositions containing the above-described compounds and their use in preparation of pharmaceuticals.

Besides having good bioactivity, the compounds of CPT derivatives of the present invention have ideal water-solubility, and high-level lactone ring stability at the physiological conditions. The CPT derivatives of the present invention also show relatively low toxicity.

DETAILED DESCRIPTION OF THE INVENTION

Figure 1:
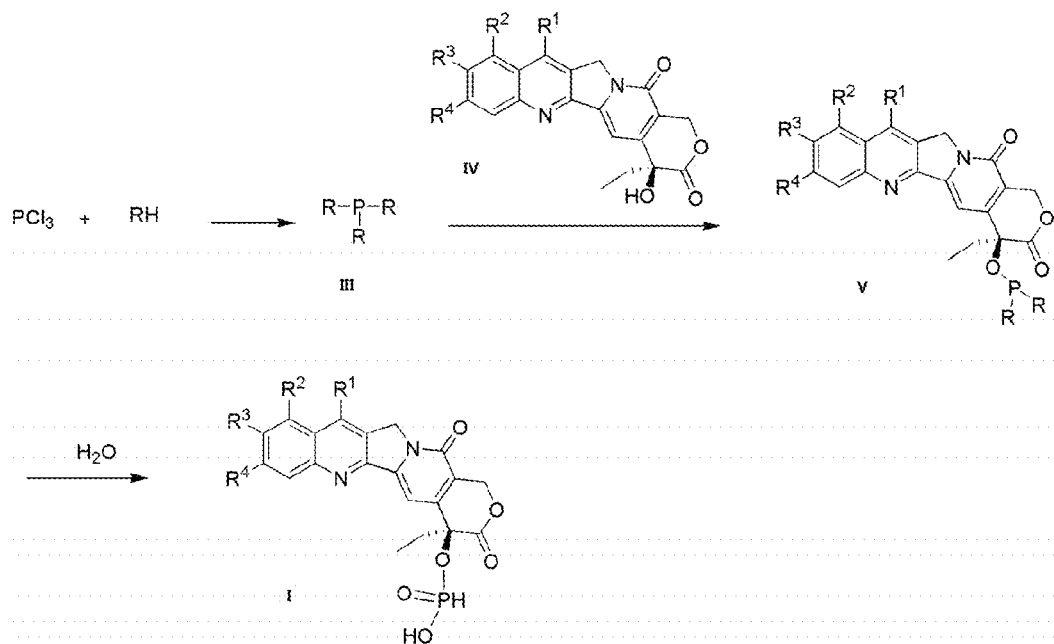
FIG. 1 shows the scheme to synthesize the camptothecin derivatives of the present invention.

Unless otherwise specified, the terms used in context of the present invention are defined as in the following text. Other terms not defined in the following text have the definitions as commonly known in the field of the present invention.

The term "CPT prodrug" refers to the camptothecin derivative with the 20(S)-hydroxyl group protected by the biodegradable protecting group. At the physiological conditions, the biodegradable protecting group of the 20(S)-hydroxyl group is slowly cleaved by specific enzymes to generate the pharmaceutically active camptothecin.

In the context, mammal includes, but not limited to, primate, especially human; rodent includes mouse, rat, and hamster; domestic animal includes rabbit, horse, cow, dog and cat etc. In some embodiments, mammal refers to human.

One aspect of the present invention relates to camptothecin phosphite of Formula I.

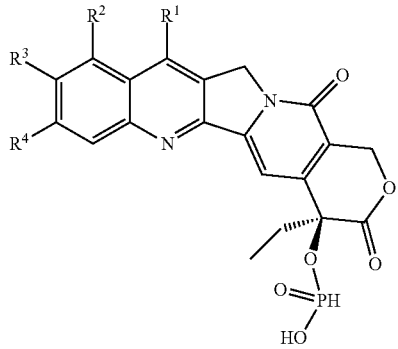

Formula I wherein $R^1$, $R^2$, $R^3$, and $R^4$ independently represent hydrogen, hydroxy, nitro, cyano, halo, carboxy, optionally substituted amino, a silicon-containing group (e.g. silyl, siloxyl, for example, containing C1-C6, but the present invention is not limited thereto), mono-ring aryloxy, C1-C6 alkoxy optionally substituted by hydroxy, nitro, cyano, halo or amino, C1-C6 alkanoyl optionally substituted by hydroxy, nitro, cyano, halo or amino, C1-C6 alkyl optionally substituted by hydroxy, nitro, cyano, halo or amino, or C3-C6 cycloalkyl optionally substituted by hydroxy, nitro, cyano, halo or amino; or $R^1$ and $R^2$ are connected via one to three other atoms to form a heterocycle, wherein the heterocycle is an N-heterocycle, S-heterocycle, O-heterocycle, or a heterocycle containing two heteroatoms selected from the group consisting of N, O and S, and $R^3$, $R^4$ independently represent hydrogen, hydroxy, nitro, cyano, halo, carboxy, optionally substituted amino, a silicon-containing group (e.g. silyl, siloxyl, for example, containing C1-C6, but the present invention is not limited thereto), mono-ring aryloxy, C1-C6 alkoxy optionally substituted by hydroxy, nitro, cyano, halo or amino, C1-C6 alkanoyl optionally substituted by hydroxy, nitro, cyano, halo or amino, C1-C6 alkyl optionally substituted by hydroxy, nitro, cyano, halo or amino, or C3-C6 cycloalkyl optionally substituted by hydroxy, nitro, cyano, halo or amino; or $R^1$, $R^2$ independently represent hydrogen, hydroxy, nitro, cyano, halo, carboxy, optionally substituted amino, a silicon-containing group (e.g. silyl, siloxyl, for example, containing C1-C6, but the present invention is not limited thereto), mono-ring aryloxy, C1-C6 alkoxy optionally substituted by hydroxy, nitro, cyano, halo or amino, C1-C6 alkanoyl optionally substituted by hydroxy, nitro, cyano, halo or amino, C1-C6 alkyl optionally substituted by hydroxy, nitro, cyano, halo or amino, or C3-C6 cycloalkyl optionally substituted by hydroxy, nitro, cyano, halo or amino, and $R^3$ and $R^4$ are oxygen atoms and connected via —O—$(CH_2)_n$—O— to form a ring, wherein n is 1 or 2.

In the above embodiments, when a substituting group contains an amino or hydroxyl group, the amino or hydroxyl group may be protected by a protecting group as commonly used in the art. Preferably, the amino protecting group is selected from benzoyl, isobutyryl, tert-butyloxycarbonyl, trityl, formyl, etc. Preferably, the hydroxyl protecting group is selected from, methyl, methoxymethyl, benzyloxymethyl, benzyl, trimethylsilyl, t-butyldimethylsilyl, acetyl, trifluoroacetyl, trimethylacetyl, benzoyl, alkylacyl, etc. Other suitable protecting groups as known to those skilled in the art are disclosed in Theodora W. Green, Peter G. M. Wuts: *Protective Groups in Organic Synthesis*, Edition 3, John Wiley & Sons (1999).

Further, preferably, the protecting group is the group which can be enzymatically cleaved at the physiological conditions, such as acyl.

Preferably, to allow CPT analogs of the present invention to exert bioactivity, $R^1$, $R^2$, $R^3$ and $R^4$ are selected from the groups of less steric hindrance to CPT, usually those with smaller molecular weight, for example, under 100.

As shown in experiments, the compounds have good drug activity and water-solubility.

A second aspect of the present invention relates to a camptothecin phosphite salt of Formula II.

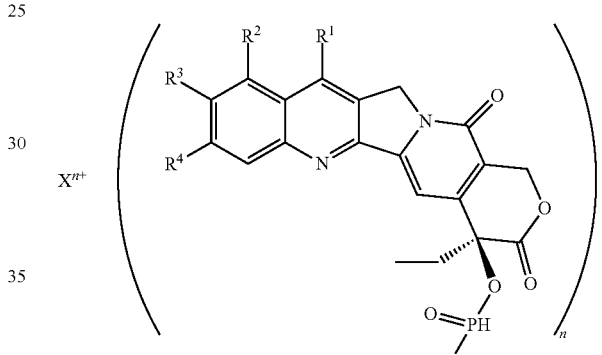

Formula II wherein $R^1$, $R^2$, $R^3$, $R^4$ are defined as above, and $X^{n+}$ is $K^+$, $Na^+$, $Li^+$, $Mg^{2+}$, $Ca^{2+}$, $Zn^{2+}$, $Fe^{3+}$, or ammonium ion, wherein the ammonium ion can be derived from one of following bases: $NH_3$, monomethylamine, dimethylamine, trimethylamine, monoethylamine, diethylamine, triethylamine, methylethylamine, dimethylethylamine, diisopropylamine, pyrrolidine, dihydro-isoindol, morpholine, N,N-diallyl amine, 4-methyl piperidine, ethanolamine, 5-bromo dihydro-isoindol, thiomorpholine, cis-2,6-dimethylmorpholine and ethylenediamine.

In addition to having good pharmaceutical activity, the salt of Formula II has desirable stability and better water solubility at the physiological conditions.

Preferably, compounds of Formula I and Formula II are derived from compounds of Formula IV as listed in Table 1 by attaching a phosphite moiety to the C-20 site.

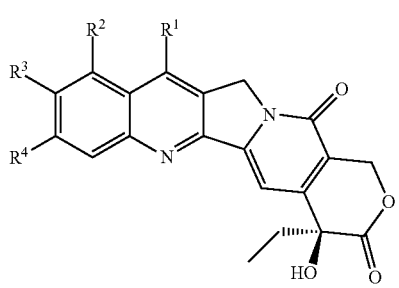

Formula IV

TABLE 1
| Compound of Formula IV | Structural Formula |
|---|---|
| Camptothecin | 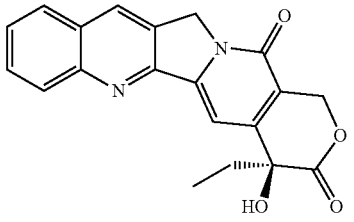 [SMILES: CC[C@@]1(O)C(=O)OCc2c1cc1n(c2=O)Cc2cc3ccccc3nc2-1] |
| SN38 | 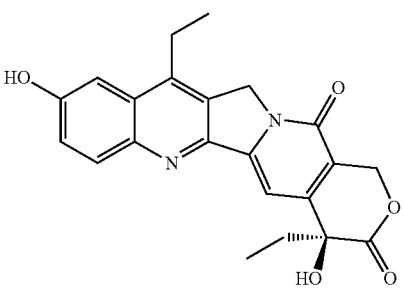 [SMILES: CCc1c2c(nc3ccc(O)cc13)-c1cc3c(c(=O)n1C2)COC(=O)[C@]3(O)CC] |
| Topotecan | 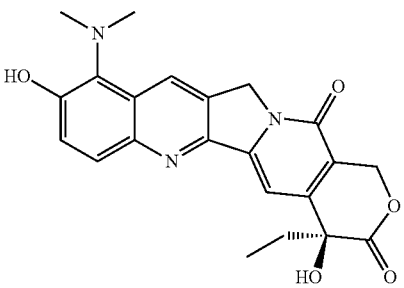 [SMILES: CC[C@@]1(O)C(=O)OCc2c1cc1n(c2=O)Cc2cc3c(N(C)C)c(O)ccc3nc2-1] |
| 9-amino-CPT | 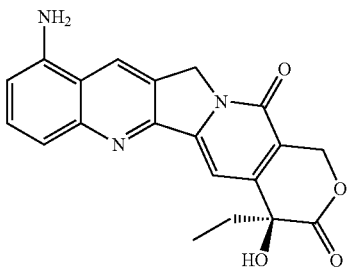 [SMILES: CC[C@@]1(O)C(=O)OCc2c1cc1n(c2=O)Cc2cc3c(N)cccc3nc2-1] |
| Irinotecan | 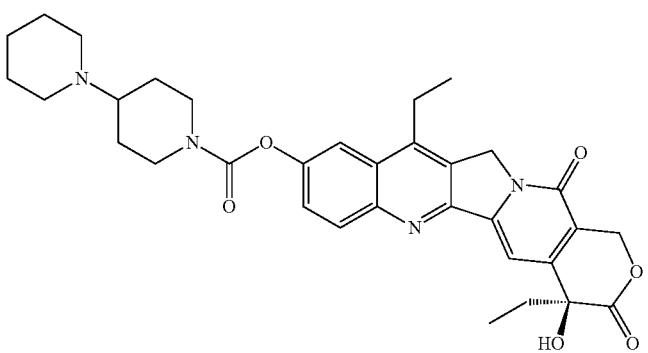 [SMILES: CCc1c2c(nc3ccc(OC(=O)N4CCC(N5CCCCC5)CC4)cc13)-c1cc3c(c(=O)n1C2)COC(=O)[C@]3(O)CC] |

TABLE 1-continued
| Compound of Formula IV | Structural Formula |
|---|---|
| 9-nitro-CPT | 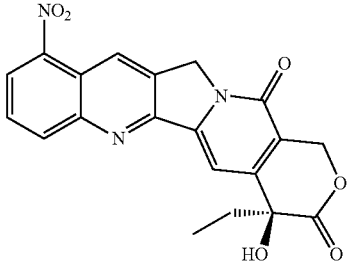 |
| Lurtotecan | 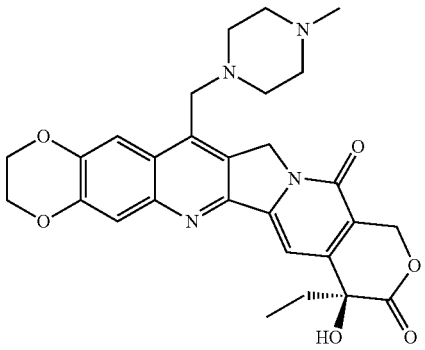 [SMILES: CC[C@@]1(O)C(=O)OCc2c1cc1n(c2=O)Cc2c-1nc1cc3c(cc1c2CN1CCN(C)CC1)OCCO3] |
| 7-ethyl-10,11-methylenedioxy-CPT | 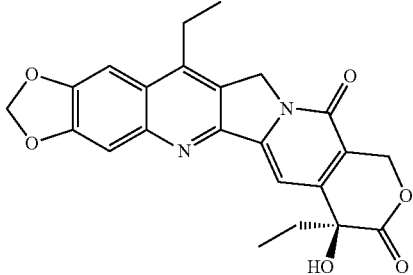 [SMILES: CCc1c2c(nc3cc4c(cc13)OCO4)-c1cc3c(c(=O)n1C2)COC(=O)[C@]3(O)CC] |
| Exatecan | 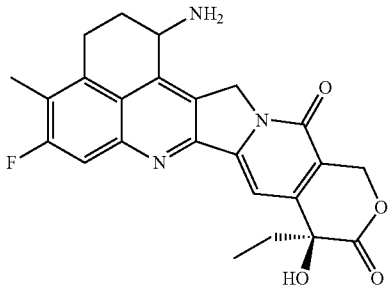 [SMILES: CC[C@@]1(O)C(=O)OCc2c1cc1n(c2=O)Cc2c-1nc1cc(F)c(C)c3c1c2C(N)CC3] |
| 7-ethyl-CPT | 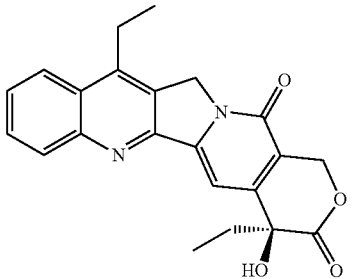 [SMILES: CCc1c2c(nc3ccccc13)-c1cc3c(c(=O)n1C2)COC(=O)[C@]3(O)CC] |

TABLE 1-continued

| Compound of Formula IV | Structural Formula |
|---|---|
| 10-Hydroxy-CPT (SN22) | |
| Gimatecan | |
| Karenitecan | |
| Silatecan | |

The compound of the present invention can be synthesized by the scheme shown in FIG. 1, including the steps of:

(1) reacting $PCl_3$ with an azole of RH, producing a phosphine triamine intermediate of Formula III:

Formula III wherein, R is

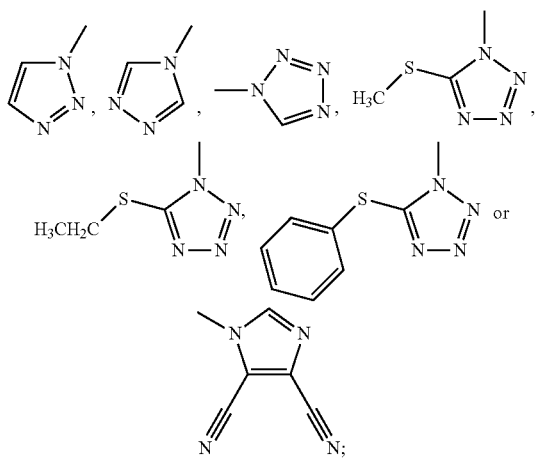

(2) reacting the phosphine triamine intermediate of Formula III with a compound of Formula IV, producing a CPT 20(S)—O-phosphoramidite precursor of Formula V:

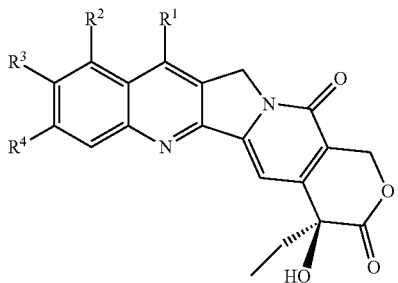

Formula IV

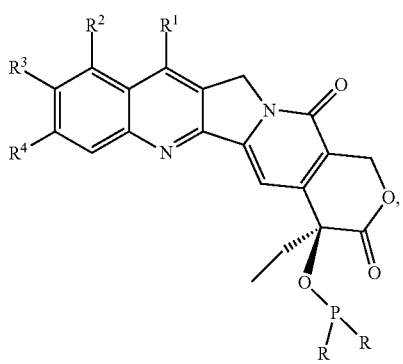

Formula V wherein $R^1$, $R^2$, $R^3$, and $R^4$ are as previously defined for Formula I, and when $R^1$, $R^2$, $R^3$, or $R^4$ is a hydroxyl group or amino group or contains the same, the hydroxyl group or the amino group is protected with a protecting group before reacting with the compound of Formula III;

(3) hydrolyzing the 20(S)—O-phosphoramidite precursor of Formula V, producing the CPT 20(S)—O— phosphite of Formula I:

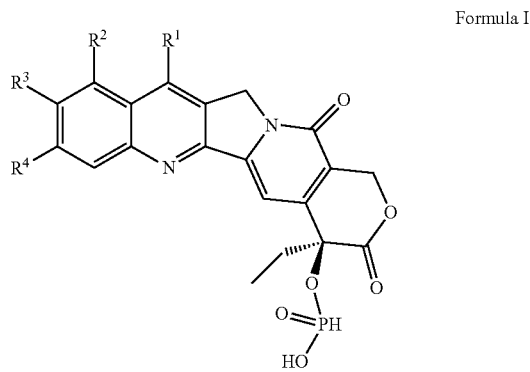

Formula I

In some embodiments, $R^1$, $R^2$, $R^3$, or $R^4$ is or contains an amino or hydroxyl group, which is protected, the protecting group is removed at this step;

(4) saltifying the compound of Formula I using a base, providing the corresponding salt. The bases that can be used in this step include, but not limited to, NaOH, $Na_2CO_3$, $NaHCO_3$, KOH, $KHCO_3$, $K_2CO_3$, LiOH, $LiHCO_3$, $Li_2CO_3$, $NH_4HCO_3$, $Ca(OH)_2$, $CaCO_3$, $Ca(HCO_3)_2$, $Mg(HCO_3)_2$, $Zn(HCO_3)_2$, $Zn(OH)_2$, and $Fe(OH)_3$, and when a quaternary ammonium salt is desired, it is possible to use the quaternary ammonium base accordingly.

The compounds of Formula I and Formula II of the present invention are effective in the treatment of mammal cancer, especially human cancer (also referred to as malignant tumor), including all forms of cancers in poorly differentiated, moderately differentiated, and well differentiated stage. In administering the compound of the present invention to patients in need of such treatment, an effective amount of the compound or formulation containing one or more compounds of the present invention is administered to the patient. As used herein, the term "effective amount" is intended to mean the amount that the compound of the present invention will result in a desirable effect. For example, for treatment on cancer/malignant tumor, the "effective amount" refers to the amount which will inhibit, or retard the development of cancer, or kill cancer or malignant cells, and/or cause the regression and/or palliation of cancer such as malignant tumors, e.g., reducing the volume or size of such tumors or eliminating the tumor entirely. The pharmaceutically effective amount or dosage is preferably between 0.1 to 100 mg of the compound of the present invention per kg of body weight. More preferably, the pharmaceutically effective amount or dosage is preferably between 0.1 to 50 mg of the compound of the present invention per kg of body weight. If necessary or feasible as deemed by a doctor or veterinarian, the effective amount may be beyond the scope mentioned above. When the compound of the present invention is administered by way of its pharmaceutically acceptable salt, solvate or hydrate, the effective amount refers to the amount of free compound.

The compound or pharmaceutical composition according to the present invention can be used in the treatment on a number of tumors and/or cancers including, but not limited to, solid tumors such as cancers of the lung, breast, colon, prostate, melanoma, pancreas, stomach, liver, brain, kidney, uterus, cervix, ovaries, urinary track, gastrointestinal, etc, as well as blood borne tumors such as leukemia, and myeloma.

The preferred solid tumors include, but are not limited to, colon and rectal cancer, breast cancer, lung cancer and myeloma, especially small-cell lung cancer.

The compound according to the present invention can be used in combination with one or more other anti-cancer drugs. The other anti-cancer drugs in the context include: 1) estrogen receptor modulator, e.g., tamoxifen, raloxifene, idoxifene; 2) androgen receptor modulator, e.g., finasteride, nilutamide, flutamide, bicalutamide; 3) retinoid receptor modulator, e.g., bexarotene, vitamin A acid, 13-cis-retinoic acid, 9-cis-retinoic acid; 4) cytotoxic substances, including alkylating agents, tumor necrosis factor, tubulin inhibitor, topoisomerase inhibitors, e.g., ifosfamide, carboplatin, ranimustine, fotemustine, oxaliplatin, mitoxantrone, paclitaxel, and topotecan; 5) anti-proliferative agents, e.g. trimetrexate, fludarabine, and capecitabine; 6) acyltransferase Inhibitors; 7) HMG-CoA reductase inhibitor; 8) HIV protease inhibitor, and 9) reverse transcriptase inhibitor, etc.

The compound of the present invention is also useful as an inhibitor of the enzyme topoisomerase I. The compound of the present invention may be administered in a dose which is effective at inhibiting the enzyme topoisomerase I. The amount is generally about 0.1-100 mg/kg of body weight per week, preferably about 1-50 mg/kg per week.

The compound of the present invention may also act as an antiviral (for example, anti-HIV) agent and antiparasitic agent.

The compound of the present invention may be administered by itself or in a pharmaceutical composition thereof. Besides the compound and pharmaceutically acceptable carriers, the composition of the present invention may include other active materials which do not impair the desired action and/or supplement the desired action.

The compounds/active materials according to the present invention can be administered by any route, for example, orally, nasally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components for injection: a sterile diluent such as water; suspensions of liposomal particles whereby the particles contain stable, active drug within the core of the particle in a pH controlled and protected environment; suspensions of liposomal particles, whose active drug is attached to the outside of the particle or either of the bilayers of the particle; saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraace-tic acid; buffers such as acetates, citrates and agents for adjusting tonicity such as sodium chloride or dextrose. The parenteral preparation can be enclosed in ampoules, disposable syringes or multiple dose vials made of glass or plastic.

Oral compositions generally include an inert diluent or an edible carrier. They may be enclosed in gelatin capsules or compressed into tablets. For the purpose of oral therapeutic administration, the aforesaid compounds may be prepared in the form of tablets, pills, capsules, troches, elixirs, suspensions, syrups, wafers, chewing gums and the like. The tablets, pills, capsules and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such a colloidal silicon dioxide; and a sweetening agent such as sucrose or saccharin; or flavoring agent such as peppermint, methyl salicylate, or orange flavoring may be added. When the dosage unit is in the form of a capsule, it may contain, in addition to material of the above type, a liquid carrier such as a fatty oil. Other dosage-unit forms may contain other various materials which modify the physical form of the dosage unit, for example, coatings. Thus tablets or pills, for example, may be coated with sugar, shellac, or other enteric coating agents. A syrup may contain, besides the active compounds, sucrose as a sweetening agent, and a preservative, a dye and a coloring agent and a flavor. Materials used in preparing these compositions should be pharmaceutically or veterinarally pure and non-toxic in the amount used.

EXAMPLE 1-1

Preparation of CPT 20(S)—O-phosphite (WQ1000)

0.69 g 1,2,4-1H-triazole (10 mmol) was dissolved in anhydrous pyridine (20 mL) and cooled to 0° C. with ice-bath, followed by addition of 0.69 g phosphorus trichloride (5 mmol). After removing the ice-bath, a solution of 3.48 g CPT in 30 ml pyridine was added with stirring at room temperature. The stirring of the reaction mixture was continued until CPT was completely consumed, then 10 ml of water was added with stirring. After the reaction was complete, the reaction solvent was evaporated under reduced pressure, and the residue was purified by a silica gel plug. The proper eluant was collected and evaporated to dryness under reduced pressure. The solid residue was redissolved in methanol or ethanol, then treated with acetone or ether dropwise to precipitate the solid. The target product WQ1000 was obtained as light-yellow powder.

M.W.: 412.33; 1H NMR (500 MHz, CDCl3): δ 8.387 (s, 1H), 8.202-8.185 (d, 1H), 7.949-7.933 (d, 1H), 7.844-7.815 (t, 1H), 7.737-6.301 (d, 1H), 7.683-7.651 (m, 2H), 5.550-5.516 (d, 1H), 5.319-5.269 (m, 3H), 2.172-2.100 (m, 1H), 2.067-1.995 (m, 1H), 0.909-0.880 (t, 3H); 13C NMR (125 MHz, CDCl3): δ 169.000, 156.489, 151.529, 147.783, 147.541, 144.449, 130.035, 129.589, 128.626, 127.397, 127.039, 126.906, 118.630, 97.542, 75.765, 65.641, 48.840, 32.789, 9.803, 6.655; 31P NMR (202 MHz, CDCl3): δ 2.26; [M+1] 413.

EXAMPLE 1-2

Preparation of CPT 20(S)—O-phosphite salt

WQ1000 was mixed with a small amount of water, then treated with saturated sodium bicarbonate solution dropwise with stirring until no air bubble generated. The solution was stirred for additional 0.5 hour after all solid was dissolved. The solution was loaded to a C18 column for chromatography. The proper eluant was collected and freeze-dried to provide the product WQ1001.

By the similar procedure, several representative compounds listed in Table 2 were prepared using Compounds of Formula IV as the starting materials. These compounds are presented as yellow solid, stable at room temperature, not easy to be oxidated and decomposed, with water-solubility more than 10 mg/mL.

TABLE 2

| Abbreviated name of substance | Compound of Formula IV | Cation | Analytical Data |
|---|---|---|---|
| WQ1001 | CPT | Na+ | M.W.: 434.31; 1H NMR (500 MHz, MeOD): δ 8.534 (s, 1H), 8.138-8.117 (d, 1H), 8.006-7.985 (d, 1H), 7.927-6.293 (d, 1H), 7.826-7.789 (t, 1H), 7.754 (s, 1H), 7.660-7.625 (s, 1H), 5.612-5.570 (d, 1H), 5.412-5.371 (d, 1H), 5.208 (s, 2H), 2.182-2.100 (m, 2H), 1.029-0.995 (t, 3H); 13C NMR (125 MHz, MeOD): δ 169.000, 156.489, 151.529, 147.783, 147.541, 144.449, 130.035, 129.589, 128.626, 127.397, 127.039, 126.906, 118.630, 97.542, 75.765, 65.641, 48.840, 32.850, 32.789, 9.803; 31P NMR (202 MHz, MeOD): δ 1.577; [M + 23] 457. |
| WQ1002 | CPT | 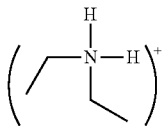 | M.W.: 485.47; 1H NMR (400 HMz, MeOD): δ 8.385 (s, 1H), 8.202-8.185 (d, 1H), 7.949-7.933 (d, 1H), 7.844-7.815 (t, 1H), 7.821-6.302 (d, 1H), 7.683-7.651 (m, 2H), 5.550-5.516 (d, 1H), 5.319-5.269 (m, 3H), 2.862-2.836 (m, 4H), 2.172-2.100 (m, 1H), 2.067-1.995 (m, 1H), 1.172-1.143 (t, 6H), 0.909-0.880 (t, 3H); 13C NMR (125 MHz, MeOD): δ 169.000, 156.489, 151.529, 147.783, 147.541, 144.449, 130.035, 129.589, 128.626, 127.397, 127.039, 126.906, 118.630, 97.542, 75.765, 65.641, 48.840, 40.508, 32.850, 32.789, 9.803, 6.655; 31P NMR (202 MHz, MeOD): δ 2.219; [M + 1] 486. |
| WQ1003 | CPT | 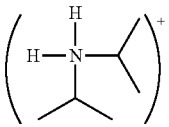 | M.W.: 513.52; 1H NMR (400 MHz, MeOD): δ 8.533 (s, 1H), 8.133-8.112 (d, 1H), 8.007-7.987 (d, 1H), 7.827-7.789 (t, 1H), 7.758 (s, 1H), 7.786-6.329 (d, 1H), 7.662-7.625 (t, 1H), 5.604-5.563 (d, 1H), 5.417-5.376 (d, 1H), 5.150 (s, 2H), 3.460-3.398 (m, 2H), 2.192-2.077 (m, 2H), 1.295-1.279 (d, 12H), 1.033-0.998 (t, 3H); 13C NMR (100 MHz, MeOD): δ 171.600, 159.255, 153.833, 151.311, 149.843, 147.188, 132.949, 131.730, 130.702, 130.232, 129.856, 129.734, 129.016, 120.289, 100.393, 78.609, 78.528, 67.720, 51.477, 34.715, 19.429, 8.375; 31P NMR (161 MHz, MeOD): δ 2.161; [M + 1] 514. |
| WQ1004 | CPT | 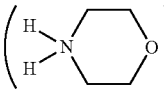 | M.W.: 499.45; 1H NMR (400 HMz, MeOD): δ 8.555 (s, 1H), 8.145-8.123 (d, 1H), 8.022-8.002 (d, 1H), 7.841-7.803 (t, 1H), 7.737 (s, 1H), 7.669-6.294 (d, 1H), 7.677-7.640 (t, 1H), 5.612-5.570 (d, 1H), 5.427-5.385 (d, 1H), 5.224 (s, 2H), 3.835-3.812 (t, 4H), 3.201-3.177 (t, 4H), 2.213-2.063 (m, 2H), 1.034-0.998 (t, 3H); 13C NMR (100 MHz, MeOD): δ 170.222, 157.703, 152.275, 149.517, 148.284, 145.728, 131.486, 130.250, 129.263, 128.641, 128.360, 128.200, 127.529, 118.849, 98.672, 77.062, 66.187, 63.493, 49.983, 43.135, 33.092, 6.793; 31P NMR (162 MHz, MeOD): δ 2.439; [M + 1] 500. |

TABLE 2-continued

| Abbreaviated name of substance | Compound of Formula IV | Cation | Analytical Data |
|---|---|---|---|
| WQ2001 | SN-38 | Na⁺ | M.W.: 478.38; 1H NMR (500 MHz, MeOD): δ 7.945-6.310 (d, 1H), 7.920-7.900 (d, 1H), 7.612 (s, 1H), 7.384-7.366 (t, 1H), 7.136-7.130 (d, 1H), 5.624-5.584 (d, 1H), 5.412-5.271 (d, 1H), 4.864-4.743 (m, 2H), 2.901-2.838 (m, 2H), 2.244-2.083 (t, 2H), 1.300-1.263 (t, 3H), 1.001-0.988 (t, 3H); 13C NMR (125 MHz, MeOD): δ 169.000, 156.489, 151.529, 147.783, 147.541, 144.449, 130.035, 129.589, 128.626, 127.397, 127.039, 126.906, 118.630, 97.542, 75.765, 65.641, 48.840, 32.850, 32.789, 18.875, 9.803; 31P NMR (202 MHz, MeOD): δ 2.476; [M + 23] 501. |
| WQ2002 | SN-38 | $NH(C_2H_5)^+$ | M.W.: 529.52; 1H NMR (500 MHz, D2O): δ 7.965-6.330 (d, 1H), 7.925-7.902 (d, 1H), 7.605 (s, 1H), 7.363-7.335 (t, 1H), 7.138-7.132 (d, 1H), 5.616-5.574 (d, 1H), 5.402-5.261 (d, 1H), 4.850-4.739 (m, 2H), 3.053-2.925 (m, 4H), 2.925-2.859 (m, 2H), 2.246-2.085 (t, 2H), 1.300-1.263 (m, 9H), 1.021-0.998 (t, 3H); 31P NMR (202 MHz, D2O): δ 2.231; [M + 1] 530. |
| WQ3001 | 10-hydroxyl CPT | Na⁺ | M.W.: 450.31; 1H NMR (500 MHz, D2O): δ 7.859-6.182 (d, 1H), 7.125-7.116 (m, 2H), 6.949 (s, 1H), 6.689-6.668 (d, 1H), 6.107 (s, 1H), 5.415-5.376 (d, 1H), 5.231-5.192 (d, 1H), 3.933-3.715 (m, 2H), 2.071-2.000 (m, 2H), 0.999-0.964 (t, 3H); 13C NMR (125 MHz, D2O): δ 171.808, 157.074, 155.121, 149.632, 146.804, 144.228, 140.809, 129.253, 128.307, 128.066, 127.421, 122.318, 117.362, 107.749, 98.311, 77.760, 66.463, 49.357, 33.031, 7.333; 31P NMR (202 MHz, D2O): δ 1.100; [M + 23] 473. |
| WQ3002 | 10-hydroxyl CPT | $NH(C_2H_5)^+$ | M.W.: 501.47; 1H NMR (500 MHz, D2O): δ 7.842-6.204 (d, 1H), 7.149-7.125 (m, 2H), 6.954 (s, 1H), 6.707-6.689 (d, 1H), 6.204 (s, 1H), 5.452-5.434 (d, 1H), 5.253-5.215 (d, 1H), 4.124-3.956 (m, 2H), 2.971-2.914 (m, 4H), 2.157-2.109 (m, 2H), 1.347-1.294 (t, 6H), 0.990-0.958 (t, 3H); 31P NMR (202 MHz, D2O): δ 1.234; [M + 1] 502. |
| WQ4001 | Topotecan | Na⁺ | M.W.: 493.38; 31P NMR (202 MHz, D2O): δ 2.141; [M + 23] 516. |
| WQ5001 | Irinotecan | Na⁺ | M.W.: 672.64; 31P NMR (202 MHz, D2O): δ 1.027; [M + 23] 695. |
| WQ6001 | 9-amino CPT | Na⁺ | M.W.: 449.33; 31P NMR (202 MHz, D2O): δ 1.546; [M + 23] 472. |
| WQ7001 | 9-nitro CPT | Na⁺ | M.W.: 479.31; 31P NMR (202 MHz, D2O): δ 1.942; [M + 23] 473. |
| WQ8001 | Lurtotecan | Na⁺ | M.W.: 604.51; 31P NMR (202 MHz, D2O): δ 1.473; [M + 23] 627. |
| WQ9001 | Exatecan | Na⁺ | M.W.: 521.41; 31P NMR (202 MHz, D2O): δ 0.315; [M + 23] 544. |
| WQ10001 | 7-ethyl CPT | Na⁺ | M.W.: 462.37; 31P NMR (202 MHz, D2O): δ 2.641; [M + 23] 473. |
| WQ11001 | 7-ethyl-10,11-methylenedioxy CPT | Na⁺ | M.W.: 506.38; 31P NMR (202 MHz, D2O): δ 1.328; [M + 23] 529. |
| WQ12001 | Gimatecan | Na⁺ | M.W.: 517.49; 31P NMR (202 MHz, D2O): δ 1.195; [M + 23] 540. |
| WQ13001 | Karenitecan | Na⁺ | M.W.: 518.59; 31P NMR (202 MHz, D2O): δ 2.347; [M + 23] 541. |
| WQ14001 | Silatecan | Na⁺ | M.W.: 532.62; 31P NMR (202 MHz, D2O): δ 2.025; [M + 23] 555. |

EXAMPLE 2

In-Vitro Anticancer Evaluation of WQ1001

Using the CellTiter-Glo kit provided by Promega Corporation, cell viability assay was performed on cancer cell lines to evaluate the ability of a compound to kill cancer cells in the in-vitro experiments. The kit measures the ATP levels by an enzymatic Luciferase assay. Normal viable cells will produce a certain level of ATP in metabolism. The enzymic reaction between the ATP product and the luciferase will emit a certain level of luminescent signal, which is captured by a luminometer and recorded as a certain luminescent read. Dead cells, with their metabolic functions diminished and no ATP produced, do not generate luminescent signals under the same measurement conditions, therefore the luminescent signal reads will be zero. When using this method to evaluate the anti-cancer activity of a compound, a certain concentration of an anti-cancer drug is added to the same amount of viable cancer cells, and the luminescent signal reading is acquired at a certain time point via CellTiter-Glo kits. Lower luminescent signal reading means lower level of viable cancer cells after treatment of the anti-cancer drug and hence stronger ability of the drug to kill the cancer cells. Detailed procedure is as follows: a certain amount of small cell lung cancer cells (ATCC catalog No. H446), breast cancer cells (ATCC catalog No. MDAMB231) or colon cancer cells (ATCC catalog No. HCT116) are seeded in 96 wells with the same cell-culture medium, then respectively treated with WQ1001 and other anti-cancer drugs for a time course of 24, 48, and 72 hours. At the respective time points, the cancer cells are mixed with CellTiter-Glo reagents for 1 hour and the corresponding luminescent signals are recorded. Since the luminescent signal reading is proportional to the amount of viable cancer cells, the luminescent signal reading can be translated into the amount of viable cancer cells correspondingly. The cell livability rate is obtained by dividing the amount of viable cancer cells after treated with a certain concentration of anti-cancer drug by the amount of viable cancer cells of the Control Group which are not treated with the drug.

Figure 2:
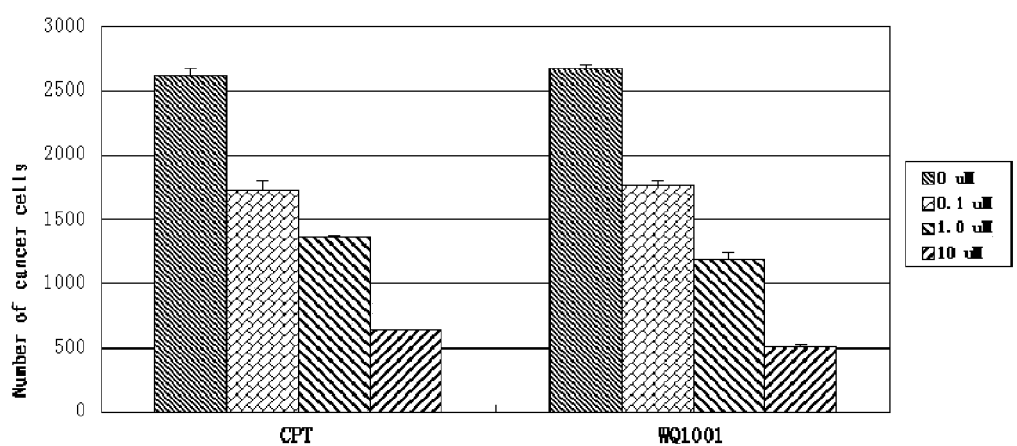
FIG. 2 shows Compound WQ1001 triggers dose-dependent cell death in H446 (small cell lung cancer) cells.
Figure 3:
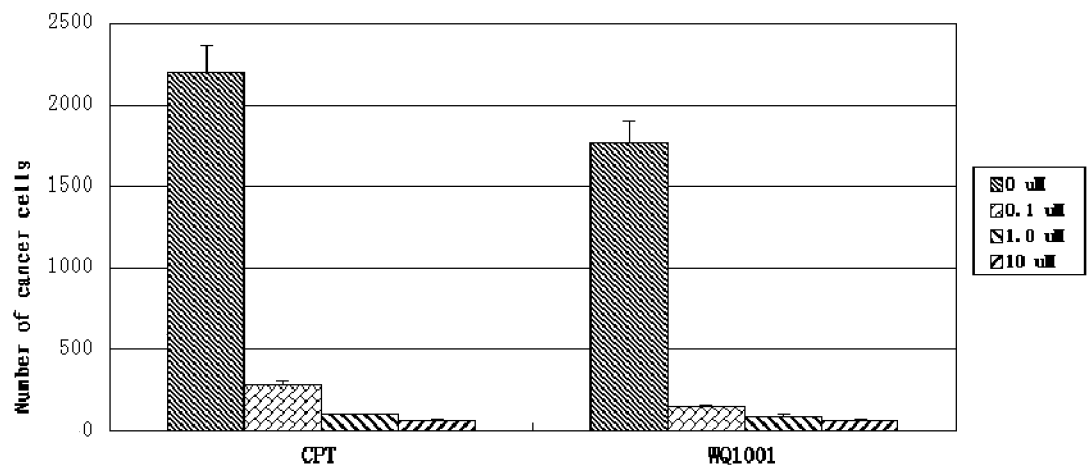
FIG. 3 shows Compound WQ1001 triggers dose-dependent cell death in MDAMB231 (breast cancer) cells.
Figure 4:
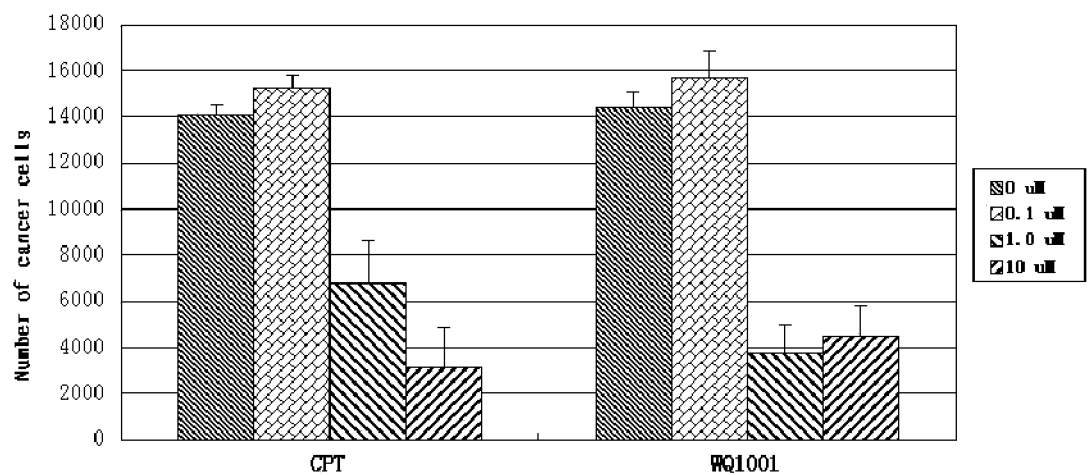
FIG. 4 shows Compound WQ1001 triggers dose-dependent cell death in HCT116 (colon cancer) cells.

The anticancer activities of compound WQ1001 are summarized in FIGS. 2-4 and Tables 3-5.

FIG. 2 shows Compound WQ1001 triggers dose-dependent cell death in H446 (small cell lung cancer) cells. In x-coordinate, the "CPT" panel represents treatment on H446 cells (small cell lung cancer) for 48 hours with CPT (dissolved in DMSO) at 4 different concentrations (0, 0.1, 1.0, 10 μM, respectively); in x-coordinate, the "WQ1001" panel represents treatment on H446 cells (small cell lung cancer) for 48 hours with WQ1001 (dissolved in saline) at 4 different concentrations (0, 0.1, 1.0, 10 μM, respectively).

TABLE 3

H446 cell viability after drug treatment for 48 hours

| Compound Conc. | CPT | WQ1001 |
| --- | --- | --- |
| 0 μM | 100% | 100% |
| 0.1 μM | 65% | 66% |
| 1.0 μM | 51% | 44% |
| 10 μM | 24% | 19% |

One can see that the water-soluble WQ1001 triggers dose-dependent cell death in H446 (small cell lung cancer) cells, and its effect is better than that of CPT.

FIG. 3 shows Compound WQ1001 triggers dose-dependent cell death in MDAMB231 (breast cancer) cells. In x-coordinate, the "CPT" panel represents treatment on MDAMB231 (breast cancer) cells for 48 hours with CPT (dissolved in DMSO) at 4 different concentrations (0, 0.1, 1.0, 10 μM, respectively). In x-coordinate, the "WQ1001" panel represents treatment on MDAMB231 (breast cancer) cells for 48 hours with WQ1001 (dissolved in saline) at 4 different concentrations (0, 0.1, 1.0, 10 μM, respectively).

TABLE 4

MDAMB231 cell viability after drug treatment

| Compound Conc. | CPT | WQ1001 |
| --- | --- | --- |
| 0 μM | 100% | 100% |
| 0.1 μM | 13% | 8% |

TABLE 4-continued

MDAMB231 cell viability after drug treatment

| Compound Conc. | CPT | WQ1001 |
| --- | --- | --- |
| 1.0 μM | 5% | 5% |
| 10 μM | 3% | 4% |

One can see that the water-soluble WQ1001 triggers dose-dependent cell death in MDAMB231 (breast cancer) cells, and its effect is comparable to that of CPT.

FIG. 4 shows Compound WQ1001 triggers dose-dependent cell death in HCT116 (colon cancer) cells. In x-coordinate, the "CPT" panel represents treatment on HCT116 (colon cancer) cells for 48 hours with CPT (dissolved in DMSO) at 4 different concentrations (0, 0.1, 1.0, 10 μM, respectively). In x-coordinate, the "WQ1001" panel represents treatment on HCT116 (colon cancer) cells for 48 hours with WQ1001 (dissolved in saline) at 4 different concentrations (0, 0.1, 1.0, 10 μM, respectively).

TABLE 5

HCT116 cell viability after drug treatment for 48 hours

| Compound Conc. | CPT | WQ1001 |
| --- | --- | --- |
| 0 μM | 100% | 100% |
| 0.1 μM | 107% | 109% |
| 1.0 μM | 76% | 26% |
| 10 μM | 11% | 31% |

One can see that the water-soluble WQ1001 triggers dose-dependent cell death in HCT116 (colon cancer) cells, and when at 1.0 μM concentration, cell viability after treatment with the test sample is significantly lower than that with reference control.

EXAMPLE 3

In-Vitro Anticancer Evaluation of WQ1002

Figure 5:
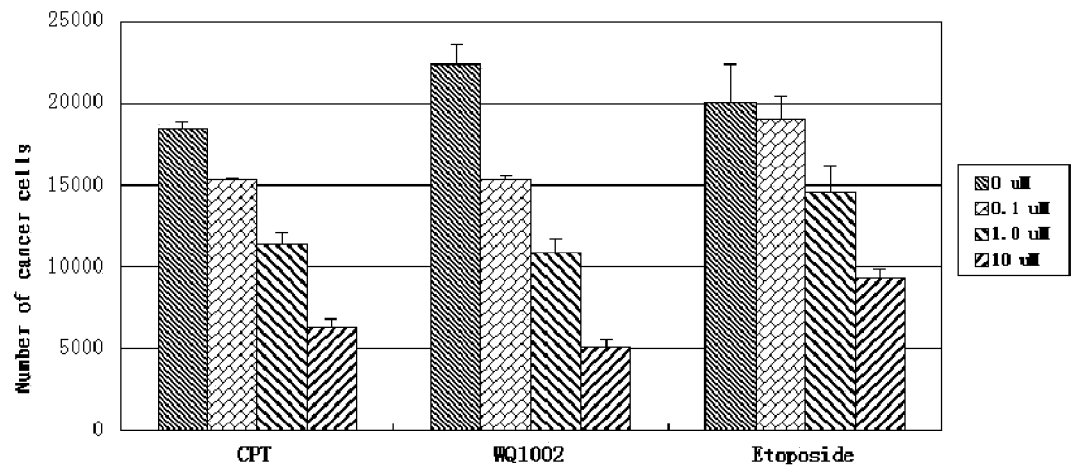
FIG. 5 shows Compound WQ1002 triggers dose-dependent cell death in H446 (small cell lung cancer) cells.
Figure 6:
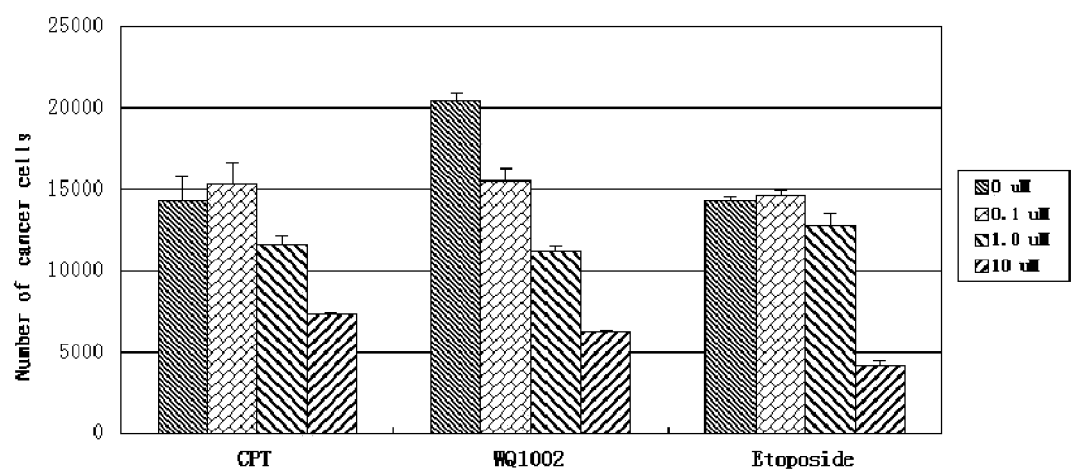
FIG. 6 shows Compound WQ1002 triggers dose-dependent cell death in HCT116 (colon cancer) cells.

By the method of Example 2, the anticancer activity of compound WQ1002 was measured, and the test results are shown in FIGS. 5-6 and Tables 6-7.

FIG. 5 shows Compound WQ1002 triggers dose-dependent cell death in H446 (small cell lung cancer) cells. In x-coordinate, the "CPT" panel represents treatment on H446 (small cell lung cancer) cells for 48 hours with CPT (dissolved in DMSO) at 4 different concentrations (0, 0.1, 1.0, 10 μM, respectively). In x-coordinate, the "WQ1002" panel represents treatment on H446 cells (small cell lung cancer) cells for 48 hours with WQ1002 (dissolved in saline) at 4 different concentrations (0, 0.1, 1.0, 10 μM, respectively). In x-coordinate, the "etoposide" panel represents treatment on H446 (small cell lung cancer) cells for 48 hours with etoposide (dissolved in saline) at 4 different concentrations (0, 0.1, 1.0, 10 μM, respectively).

TABLE 6

H446 cell viability after drug treatment for 48 hours

| Compound Conc. | CPT | WQ1002 | etoposide |
| --- | --- | --- | --- |
| 0 μM | 100% | 100% | 100% |
| 0.1 μM | 65% | 68% | 95% |
| 1.0 μM | 51% | 48% | 73% |
| 10 μM | 24% | 23% | 47% |

One can see that the water-soluble WQ1002 triggers dose-dependent cell death in H446 (small cell lung cancer) cells and its effect is better than those of CPT and etoposide (already used in clinical application, targeting topoisomerase II).

FIG. 6 shows Compound WQ1002 triggers dose-dependent cell death in HCT116 (colon cancer) cells. In x-coordinate, the "CPT" panel represents treatment on HCT116 (colon cancer) cells for 48 hours with CPT (dissolved in DMSO) at 4 different concentrations (0, 0.1, 1.0, 10 μM, respectively). In x-coordinate, the "WQ1002" panel represents treatment on HCT116 (colon cancer) cells for 48 hours with WQ1002 (dissolved in saline) at 4 different concentrations (0, 0.1, 1.0, 10 μM, respectively). In x-coordinate, the "etoposide" panel represents treatment on HCT116 (colon cancer) cells for 48 hours with etoposide (dissolved in saline) at 4 different concentrations (0, 0.1, 1.0, 10 μM, respectively).

TABLE 7

HCT116 cell viability after drug treatment for 48 hours

| Compound Conc. | CPT | WQ1002 | etoposide |
|---|---|---|---|
| 0 μM | 100% | 100% | 100% |
| 0.1 μM | 107% | 76% | 102% |
| 1.0 μM | 82% | 55% | 89% |
| 10 μM | 51% | 31% | 29% |

One can see that the water-soluble WQ1002 triggers dose-dependent cell death in HCT116 (colon cancer) cells and its effect is better than those of CPT and etoposide (already used in clinical application, targeting topoisomerase II).

EXAMPLES 4 AND 5

In-Vitro Anticancer Evaluation of WQ1003 and WQ1004

Figure 7:
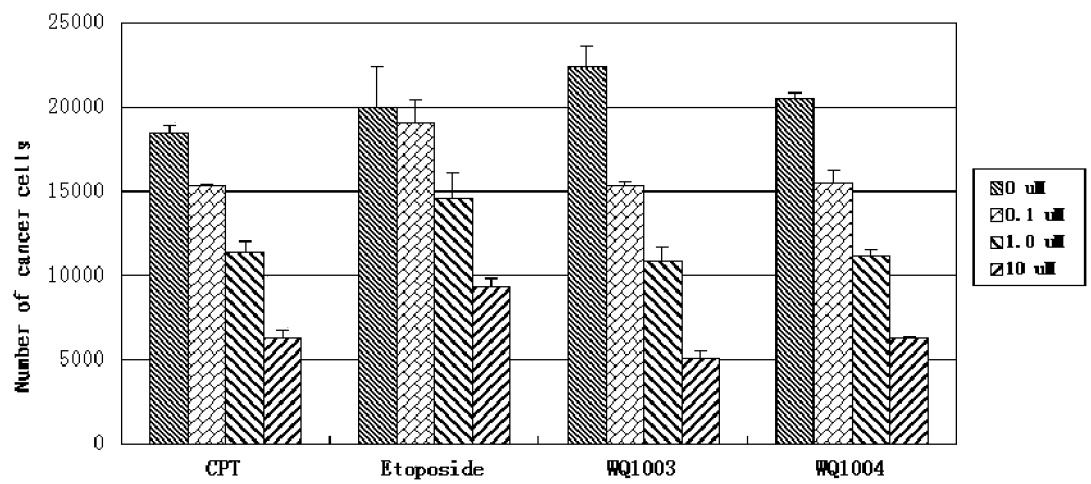
FIG. 7 shows Compound WQ1003 and WQ1004 trigger dose-dependent cell death in H446 (small cell lung cancer) cells.

By the method of Example 2, the anticancer activity of Compounds WQ1003 and WQ1004 was measured, and the test results are shown in FIG. 7 and Table 8.

FIG. 7 shows Compounds WQ1003 and WQ1004 trigger dose-dependent cell death in H446 (small cell lung cancer) cells. In x-coordinate, the "CPT" panel represents treatment on H446 (small cell lung cancer) cells for 48 hours with CPT (dissolved in DMSO) at 4 different concentrations (0, 0.1, 1.0, 10 μM, respectively). In x-coordinate, the "etoposide" panel represents treatment on H446 (small cell lung cancer) cells for 48 hours with etoposide (dissolved in saline) at 4 different concentrations (0, 0.1, 1.0, 10 μM, respectively). In x-coordinate, the "WQ1003" panel represents treatment on H446 (small cell lung cancer) cells for 48 hours with WQ1003 (dissolved in saline) at 4 different concentrations (0, 0.1, 1.0, 10 μM, respectively). In x-coordinate, the "WQ1004" panel represents treatment on H446 (small cell lung cancer) cells for 48 hours with WQ1004 (dissolved in saline) at 4 different concentrations (0, 0.1, 1.0, 10 μM, respectively).

TABLE 8

H446 cell viability after drug treatment for 48 hours

| Compound Conc. | CPT | etoposide | WQ1003 | WQ1004 |
|---|---|---|---|---|
| 0 μM | 100% | 100% | 100% | 100% |
| 0.1 μM | 65% | 95% | 66% | 71% |
| 1.0 μM | 51% | 73% | 46% | 57% |
| 10 μM | 24% | 47% | 23% | 25% |

One can see that the water-soluble WQ1003 and WQ1004 trigger dose-dependent cell death in H446 (small cell lung cancer) cells and their effects are better than that of CPT and that of etoposide (already used in clinical application, targeting topoisomerase II) as well.

EXAMPLES 6 AND 7

In Vitro Anticancer Evaluation of WQ2001 and WQ2002

Figure 8:
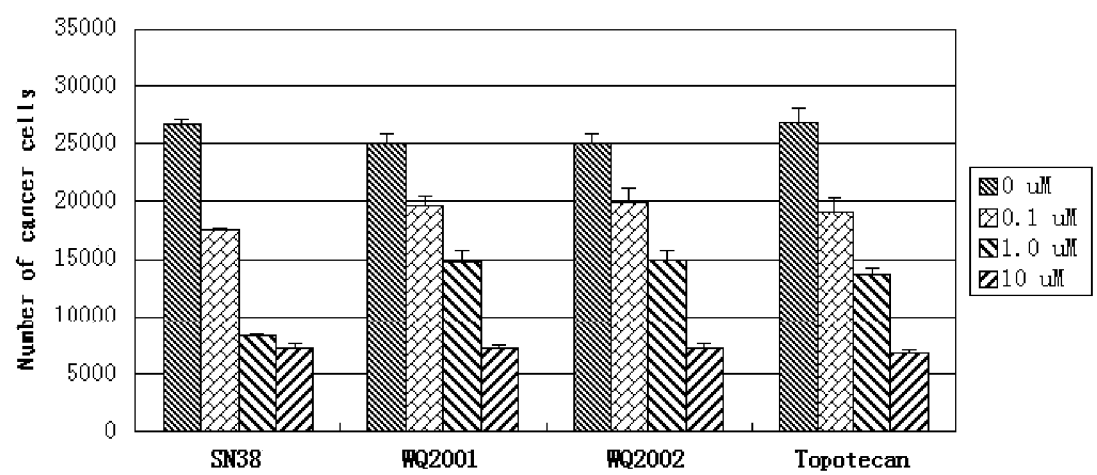
FIG. 8 shows Compound WQ2001 and WQ2002 trigger dose-dependent cell death in H446 (small cell lung cancer) cells.
Figure 9:
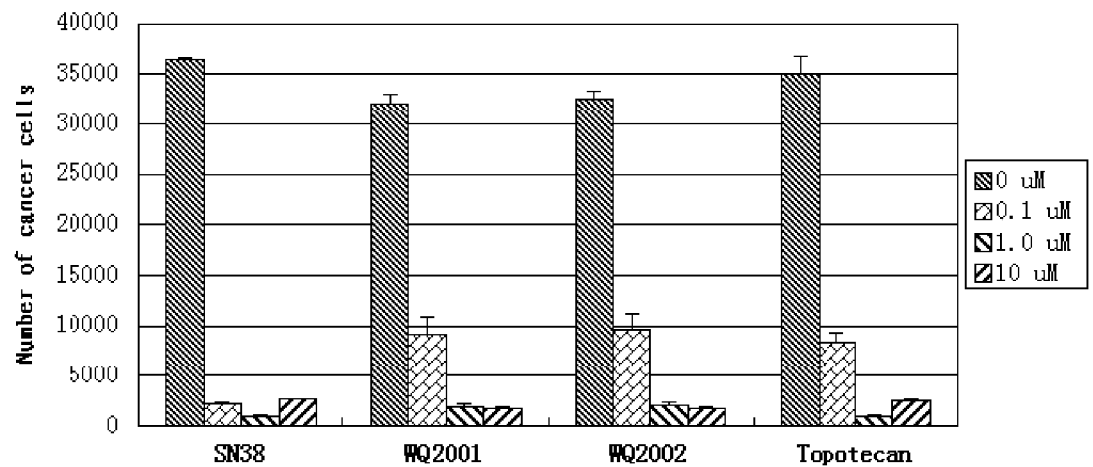
FIG. 9 shows Compound WQ2001 and WQ2002 trigger dose-dependent cell death in HCT116 (colon cancer) cells.
Figure 10:
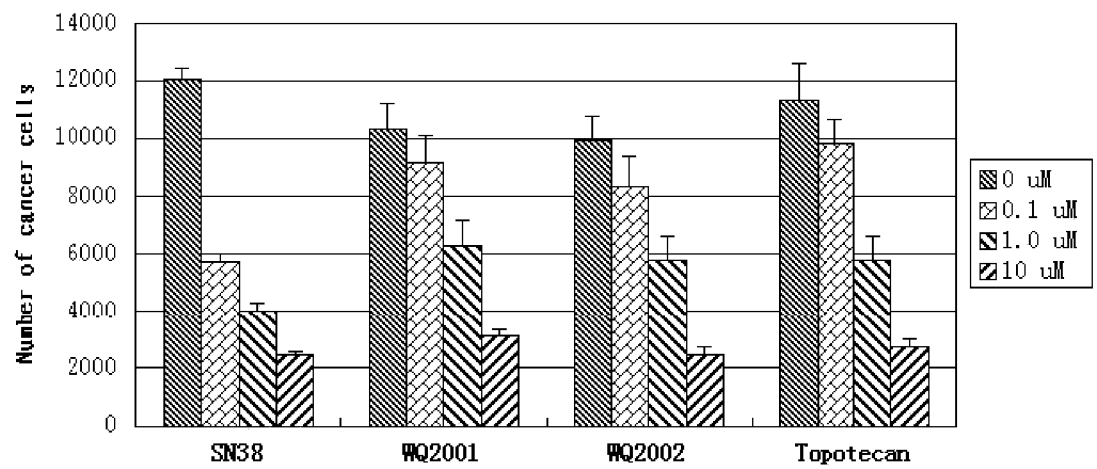
FIG. 10 shows Compound WQ2001 and WQ2002 trigger dose-dependent cell death in MDAMB231 (breast cancer) cells.

By the method of Example 2, the anticancer activity of compounds WQ2001 and WQ2002 was measured, and the test results are shown in FIGS. 8-10 and Tables 9-11.

FIG. 8 shows compounds WQ2001 and WQ2002 trigger dose-dependent cell death in H446 (small cell lung cancer) cells. In x-coordinate, the "SN38" panel represents treatment on H446 (small cell lung cancer) cells for 48 hours with SN38 (dissolved in DMSO) at 4 different concentrations (0, 0.1, 1.0, 10 μM, respectively). In x-coordinate, the "topotecan" panel represents treatment on H446 (small cell lung cancer) cells for 48 hours with topotecan (dissolved in saline) at 4 different concentrations (0, 0.1, 1.0, 10 μM, respectively). In x-coordinate, the "WQ2001" panel represents treatment on H446 (small cell lung cancer) cells for 48 hours with WQ2001 (dissolved in saline) at 4 different concentrations (0, 0.1, 1.0, 10 μM, respectively). In x-coordinate, the "WQ2002" panel represents treatment on H446 (small cell lung cancer) cells for 48 hours with WQ2002 (dissolved in saline) at 4 different concentrations (0, 0.1, 1.0, 10 μM, respectively).

TABLE 9

H446 cell viability after drug treatment for 48 hours

| Compound Conc. | SN38 | WQ2001 | WQ2002 | Topotecan |
|---|---|---|---|---|
| 0 μM | 100% | 100% | 100% | 100% |
| 0.1 μM | 79% | 78% | 79% | 73% |
| 1.0 μM | 60% | 59% | 59% | 50% |
| 10 μM | 28% | 28% | 28% | 25% |

One can see that the water-soluble WQ2001 and WQ2002 trigger dose-dependent cell death in H446 (small cell lung cancer) cells and their effects are comparable with those of SN38 and topotecan (already used in clinical application, targeting topoisomerase I).

FIG. 9 shows Compounds WQ2001 and WQ2002 trigger dose-dependent cell death in HCT116 (colon cancer) cells. In x-coordinate, the "SN38" panel represents treatment on HCT116 (colon cancer) cells for 48 hours with SN38 (dissolved in DMSO) at 4 different concentrations (0, 0.1, 1.0, 10 μM, respectively). In x-coordinate, the "topotecan" panel represents treatment on HCT116 (colon cancer) cells for 48 hours with topotecan (dissolved in saline) at 4 different concentrations (0, 0.1, 1.0, 10 μM, respectively). In x-coordinate, the "WQ2001" panel represents treatment on HCT116 (colon cancer) cells for 48 hours with WQ2001 (dissolved in saline) at 4 different concentrations (0, 0.1, 1.0, 10 μM, respectively). In x-coordinate, the "WQ2002" panel represents treatment on HCT116 (colon cancer) cells for 48 hours with WQ2002 (dissolved in saline) at 4 different concentrations (0, 0.1, 1.0, 10 μM, respectively).

TABLE 10

HCT116 cell viability after drug treatment for 48 hours

| Compound Conc. | SN38 | WQ2001 | WQ2002 | Topotecan |
|---|---|---|---|---|
| 0 μM | 100% | 100% | 100% | 100% |
| 0.1 μM | 5% | 30% | 29% | 26% |
| 1.0 μM | 2% | 4% | 4% | 2% |
| 10 μM | 6% | 3% | 3% | 6% |

One can see that Compounds WQ2001 and WQ2002 trigger dose-dependent cell death in HCT116 (colon cancer) cells and their effects are comparable with those of SN38 and topotecan (already used in clinical application, targeting topoisomerase I), both having good effect.

FIG. 10 shows compounds WQ2001 and WQ2002 trigger dose-dependent cell death in MDAMB231 (breast cancer) cells. In x-coordinate, the "SN38" panel represents treatment on MDAMB231 cells for 48 hours with SN38 (dissolved in DMSO) at 4 different concentrations (0, 0.1, 1.0, 10 μM, respectively). The "topotecan" panel represents treatment on MDAMB231 cells for 48 hours with topotecan (dissolved in saline) at 4 different concentrations (0, 0.1, 1.0, 10 μM, respectively). In x-coordinate, the "WQ2001" panel represents treatment on MDAMB23 cells for 48 hours with WQ2001 (dissolved in saline) at 4 different concentrations (0, 0.1, 1.0, 10 μM, respectively). In x-coordinate, the "WQ2002" panel represents treatment on MDAMB23 cells for 48 hours with WQ2002 (dissolved in saline) at 4 different concentrations (0, 0.1, 1.0, 10 μM, respectively). The test results are listed in Table 11.

TABLE 11

MDAMB231 cell viability after drug treatment for 48 hours

| Compound Conc. | SN38 | WQ2001 | WQ2002 | Topotecan |
|---|---|---|---|---|
| 0 μM | 100% | 100% | 100% | 100% |
| 0.1 μM | 48% | 73% | 85% | 68% |
| 1.0 μM | 33% | 59% | 58% | 50% |
| 10 μM | 20% | 28% | 26% | 23% |

One can see that the water-soluble WQ2001 and WQ2002 trigger dose-dependent cell death in MDAMB23 cells and their effects are slightly lower than that of SN38 but comparable with that of topotecan (already used in clinical application, targeting topoisomerase I).

EXAMPLES 8 AND 9

In Vitro Anticancer Evaluation of WQ3001 and WQ3002

Figure 11:
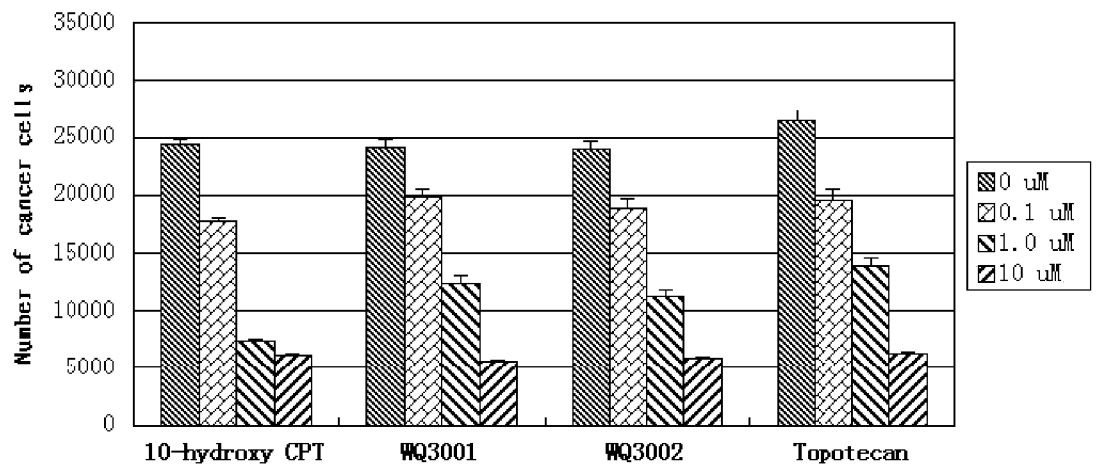
FIG. 11 shows Compound WQ3001 and WQ3002 trigger dose-dependent cell death in H446 (small cell lung cancer) cells.
Figure 12:
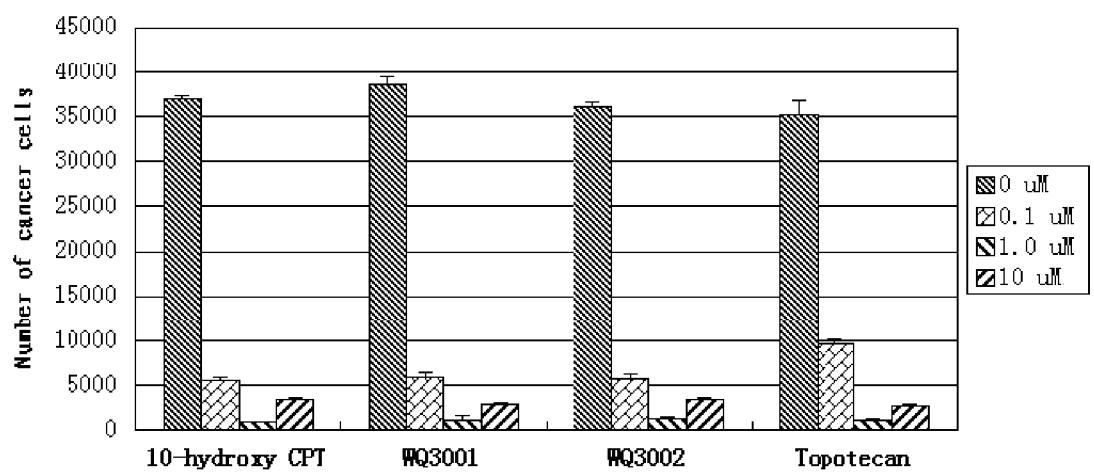
FIG. 12 shows compounds WQ3001 and WQ3002 trigger dose-dependent cell death in HCT116 (colon cancer) cells.
Figure 13:
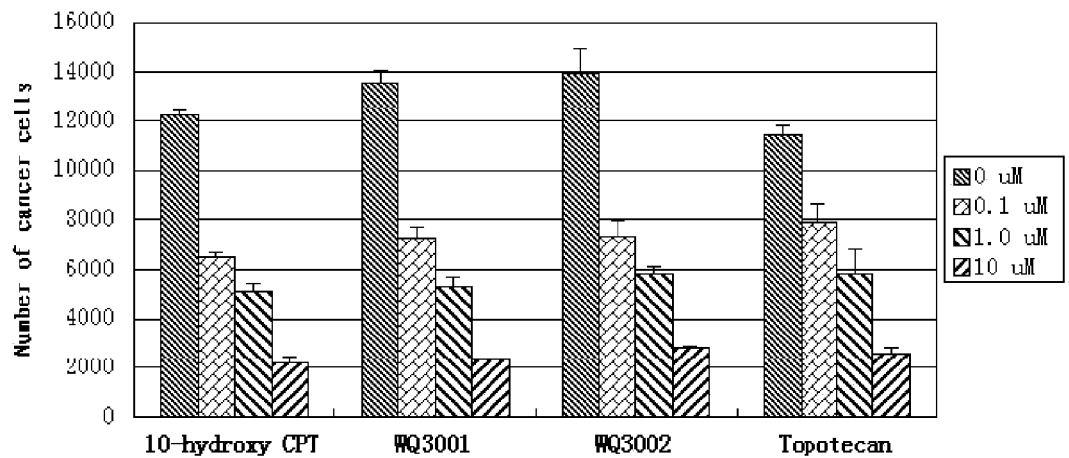
FIG. 13 shows Compound WQ3001 and WQ3002 trigger dose-dependent cell death in MDAMB231 (breast cancer) cells.

By the method of Example 2, the anticancer activity of compounds WQ3001 and WQ3002 was measured, and the test results are shown in FIGS. 11-13 and Tables 12-14.

FIG. 11 and Table 12 show Compound WQ3001 and WQ3002 trigger dose-dependent cell death in H446 (small cell lung cancer) cells. In x-coordinate, the "10-hydroxyl CPT" panel represents treatment on H446 (small cell lung cancer) cells for 48 hours with "10-hydroxyl CPT" (dissolved in DMSO) at 4 different concentrations (0, 0.1, 1.0, 10 μM, respectively). In x-coordinate, the "topotecan" panel represents treatment on H446 (small cell lung cancer) cells for 48 hours with topotecan (dissolved in saline) at 4 different concentrations (0, 0.1, 1.0, 10 μM, respectively). In x-coordinate, the "WQ3001" panel represents treatment on H446 (small cell lung cancer) cells for 48 hours with WQ3001 (dissolved in saline) at 4 different concentrations (0, 0.1, 1.0, 10 μM, respectively). In x-coordinate, the "WQ3002" panel represents treatment on H446 (small cell lung cancer) cells for 48 hours with WQ3002 (dissolved in saline) at 4 different concentrations (0, 0.1, 1.0, 10 μM, respectively).

TABLE 12

H446 cell viability after drug treatment for 48 hours

| Compound Conc. | 10-hydroxyl CPT | WQ3001 | WQ3002 | Topotecan |
|---|---|---|---|---|
| 0 μM | 100% | 100% | 100% | 100% |
| 0.1 μM | 72% | 83% | 79% | 73% |
| 1.0 μM | 30% | 51% | 47% | 50% |
| 10 μM | 24% | 23% | 25% | 23% |

One can see that WQ3001 and WQ3002 trigger dose-dependent cell death in H446 (small cell lung cancer) cells and their effects are comparable with those of 10-hydroxyl CPT and topotecan (already used in clinical application, targeting topoisomerase I).

FIG. 12 and Table 13 show Compounds WQ3001 and WQ3002 trigger dose-dependent cell death in HCT116 (colon cancer) cells. In x-coordinate, the "10-hydroxyl CPT" panel represents treatment on HCT116 (colon cancer) cells for 48 hours with 10-hydroxyl CPT (dissolved in DMSO) at 4 different concentrations (0, 0.1, 1.0, 10 μM, respectively). In x-coordinate, the "topotecan" panel represents treatment on HCT116 (colon cancer) cells for 48 hours with topotecan (dissolved in saline) at 4 different concentrations (0, 0.1, 1.0, 10 μM, respectively). In x-coordinate, the "WQ3001" panel represents treatment on HCT116 (colon cancer) cells for 48 hours with WQ3001 (dissolved in saline) at 4 different concentrations (0, 0.1, 1.0, 10 μM, respectively). In x-coordinate, the "WQ3002" panel represents treatment on HCT116 (colon cancer) cells for 48 hours with WQ3002 (dissolved in saline) at 4 different concentrations (0, 0.1, 1.0, 10 μM, respectively).

TABLE 13

HCT116 cell viability after drug treatment for 48 hours

| Compound Conc. | 10-hydroxyl CPT | WQ3001 | WQ3002 | Topotecan |
|---|---|---|---|---|
| 0 μM | 100% | 100% | 100% | 100% |
| 0.1 μM | 15% | 15% | 15% | 26% |
| 1.0 μM | 1% | 2% | 2% | 2% |
| 10 μM | 9% | 6% | 9% | 6% |

One can see that WQ3001 and WQ3002 trigger dose-dependent cell death in HCT116 (colon cancer) cells and their effects are comparable with those of 10-hydroxyl CPT and topotecan (already used in clinical application, targeting topoisomerase I).

FIG. 13 and Table 14 show Compounds WQ3001 and WQ3002 trigger dose-dependent cell death in MDAMB231 (breast cancer) cells. In x-coordinate, the "10-hydroxyl CPT" panel represents treatment on MDAMB231 (breast cancer) cells for 48 hours with 10-hydroxyl CPT (dissolved in DMSO) at 4 different concentrations (0, 0.1, 1.0, 10 μM, respectively). In x-coordinate, the "topotecan" panel represents treatment on MDAMB231 (breast cancer) cells for 48 hours with topotecan (dissolved in saline) at 4 different concentrations (0, 0.1, 1.0, 10 μM, respectively). In x-coordinate, the "WQ3001" panel represents treatment on MDAMB23 cells for 48 hours with WQ3001 (dissolved in saline) at 4 different concentrations (0, 0.1, 1.0, 10 μM, respectively). In x-coordinate, the "WQ3002" panel represents treatment on MDAMB23 cells for 48 hours with WQ3002 (dissolved in saline) at 4 different concentrations (0, 0.1, 1.0, 10 μM, respectively).

TABLE 14

MDAMB231 cell viability after drug treatment for 48 hours

| Compound Conc. | 10-hydroxyl CPT | WQ3001 | WQ3002 | Topotecan |
|---|---|---|---|---|
| 0 μM | 100% | 100% | 100% | 100% |
| 0.1 μM | 53% | 51% | 51% | 68% |
| 1.0 μM | 40% | 37% | 41% | 50% |
| 10 μM | 18% | 17% | 20% | 23% |

One can see that the water-soluble WQ3001 and WQ3002 trigger dose-dependent cell death in MDAMB23 cells and their effects are comparable with those of 10-hydroxyl CPT and topotecan (already used in clinical application, targeting topoisomerase I).

Table 15 lists comparison of properties between the representative compounds of the present invention and several existing CPT derivatives. In the test, the lactone ring stability was characterized by lactone ring conservation rate measured by HPLC (liquid chromatogram) after placing the test compounds in buffer solution of pH 7.4. The anticancer activity was characterized by viability of H446 cancer cells at 10 μM drug concentration. From the Table, one can learn the differences in water-solubility, lactone ring stability and toxicology of the compounds of the present invention.

TABLE 15

Comparison of bioactivity and physical properties between the representative compounds of the present invention and those of the control compounds

| Test substance | Water-solubility | Lactone ring stability | Cancer cell viability |
|---|---|---|---|
| CPT | <0.1 mg/mL | <50% | <30% |
| topotecan | 1 mg/mL | <50% | >30% |
| irinotecan | 1 mg/mL | <50% | >30% |
| CPT-20(S)-phosphate | >10 mg/mL | >90% | >85% |
| WQ1001 | >10 mg/mL | >90% | <30% |
| WQ1002 | >10 mg/mL | >90% | <30% |
| WQ1003 | >10 mg/mL | >90% | <30% |
| WQ1004 | >10 mg/mL | >90% | <30% |
| WQ2001 | >10 mg/mL | >90% | <30% |
| WQ2002 | >10 mg/mL | >90% | <30% |
| WQ3001 | >10 mg/mL | >90% | <30% |
| WQ3002 | >10 mg/mL | >90% | <30% |
| WQ4001 | >10 mg/mL | >90% | <30% |
| WQ5001 | >10 mg/mL | >90% | <30% |
| WQ6001 | >10 mg/mL | >90% | <30% |
| WQ7001 | >10 mg/mL | >90% | <30% |
| WQ8001 | >10 mg/mL | >90% | <30% |
| WQ9001 | >10 mg/mL | >90% | <30% |
| WQ10001 | >10 mg/mL | >90% | <30% |
| WQ11001 | >10 mg/mL | >90% | <30% |
| WQ12001 | >10 mg/mL | >90% | <30% |
| WQ13001 | >10 mg/mL | >90% | <30% |
| WQ14001 | >10 mg/mL | >90% | <30% |

EXAMPLE 10

Animal Study on Anticancer Evaluation Using the Human Small Cell Lung Cancer NCI-H446 Nude Mouse Xenograft Model The human small cell lung cancer NCI-H446 cells were grafted to nude mice. When the volume of the tumor grew to about 100 mm$^3$, the mice were randomly divided into 5 groups by the stratified tumor volumes: the Negative Control Group, three groups for WQ1001 (Low Dosage Group, Medium Dosage Group, and High Dosage Group), and the Positive Control Group (topotecan). The drugs were administered by intravenous injection. Detailed scheme of drug administration is shown in Table 16. The day of first drug administration is recorded as D0. The body weight was measured before each drug administration, and the drug amount was adjusted according to the body weight. After stopping the administering drug, the body weights are measured twice weekly. At the end of the test (D22), the body weights were measured right before sacrificing the animals.

TABLE 16

Drug administration scheme of the in vivo antitumor drug efficacy study of WQ1001 using the human small cell lung cancer NCI-H446 nude mouse xenograft model

| Group | Animal count | Dosage (mg/kg) | Drug conc. (mg/ml) | Drug administration path & times | Volume of drug administration (ml/20 g) |
|---|---|---|---|---|---|
| Negative Control Group (NS) | 10 | / | / | D0, 2, 4, 11, 13, 15 | 0.2 |
| Test Group (WQ1001) Low Dosage Group | 8 | 10 | 1.0 | D0, 2, 4, 11, 13, 15 | 0.2 |
| Medium Dosage Group | 8 | 20 | 2.0 | D0, 2, 4, 11, 13, 15 | 0.2 |
| High Dosage Group | 8 | 40 | 4.0 | D0, 2, 4, 11, 13, 15 | 0.2 |
| Positive Control Group (topotecan) | 8 | 10 | 1.0 | D0, 4, 7, 11, 14, 17 | 0.2 |

The drug was administrated right after the group division. The results of body weight change showed that the body weights of the WQ1001 10 mg/kg Group were normal; the animal body weights of the WQ1001 20 mg/kg and 40 mg/kg Groups decreased significantly one week after being administered with the drug, but returned to normal after stopping the drug for 5 days; the animal body weights of the WQ1001 40 mg/kg Group and the topotecan 10 mg/kg Group decreased significantly at the end of test (D22), but no animal death appeared. The drug dosages of the WQ1001 40 mg/kg Group and the topotecan 10 mg/kg Group have reached their MTD (Maximum Toxicity Dosage) respectively.

At the end of the test, tumor growths of all drug-treated groups were slower than that of the Negative Control Group. WQ1001 was administered by I.V. injection once every other day for 3 consecutive times, followed by 7 days' rest without drug administration, then one more circle was performed, for a total of 6 times of administration. Administering 10 mg/kg, 20 mg/kg and 40 mg/kg all inhibited tumor growth, and the 40 mg/kg efficacy was the best. Administering topotecan 10 mg/kg twice weekly in interval of 2-3 days for 3 weeks (6 times) significantly inhibited tumor growth, with efficacy comparable to that of WQ1001 10 mg/kg or 20 mg/kg.

Figure 14:
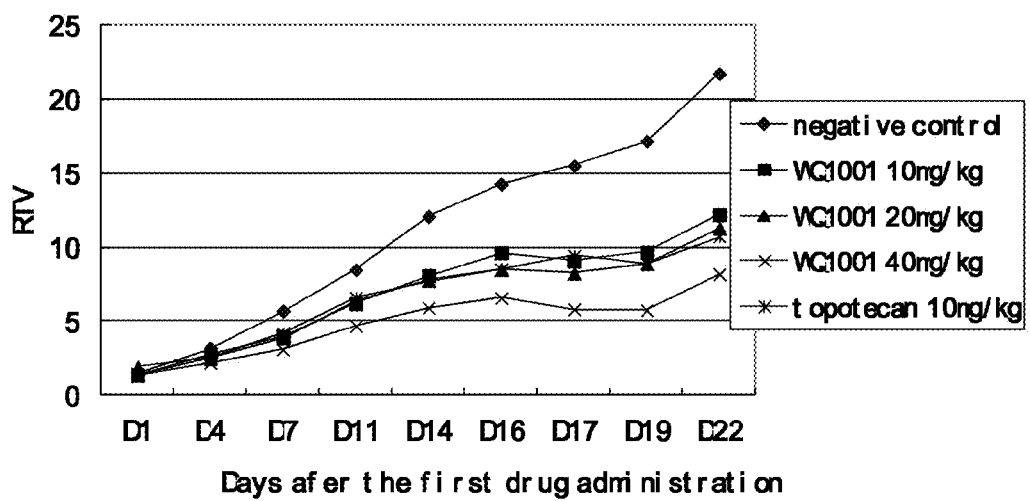
FIG. 14 shows relative change of tumor volumes in the in-vivo anti-tumor experiments of WQ1001 using the human small cell lung cancer NCI-H446 nude mouse xenograft model.

It can be concluded from the study of animal toxicity (animal body-weight change) and antitumor efficacy that: under the condition of similar antitumor efficacy, WQ1001 is less toxic to animal than topotecan. The test results are detailed in Table 17 and FIG. 14.

In Table 17, RTV means Relative Tumor Volume, as calculated by $V_t/V_0$, wherein $V_0$ is the tumor volume measured at day D0, and $V_t$ is the tumor volume of each measurement. The evaluation indicator of antitumor efficacy is Relative Tumor Growth Rate T/C(%)=$(T_{RTV}/C_{RTV})\times 100\%$, wherein $T_{RTV}$ is the RTV of the treatment group, and $C_{RTV}$ is the RTV of the Negative Control Group.

TABLE 17

Body-weight change and tumor inhibition effects of all groups in the WQ1001 in vivo antitumor efficacy test

| Group | Drug administration schedule | Animal body-weight (g) Start | End | $RTV_{22}$ | $T_{22}/C_{22}$ (%) |
|---|---|---|---|---|---|
| Negative Control Group | D0, 2, 4, 11, 13, 15 | 17.0 ± 1.0 | 18.9 ± 1.3 | 21.8 ± 10.2 | 100 |
| WQ1001 10 mg/kg | D0, 2, 4, 11, 13, 15 | 17.4 ± 1.1 | 18.6 ± 1.4 | 12.2 ± 5.1 | 56.2 |
| WQ1001 20 mg/kg | D0, 2, 4, 11, 13, 15 | 16.8 ± 1.3 | 17.6 ± 1.4 | 11.3 ± 4.0 | 52.0 |
| WQ1001 40 mg/kg | D0, 2, 4, 11, 13, 15 | 16.9 ± 1.2 | 15.4 ± 1.6** | 8.2 ± 4.3** | 37.7 |
| Topotecan 10 mg/kg | D0, 4, 7, 11, 14, 17 | 17.6 ± 1.2 | 16.4 ± 1.5** | 10.7 ± 4.8* | 49.3 |

EXAMPLE 11

Figure 15:
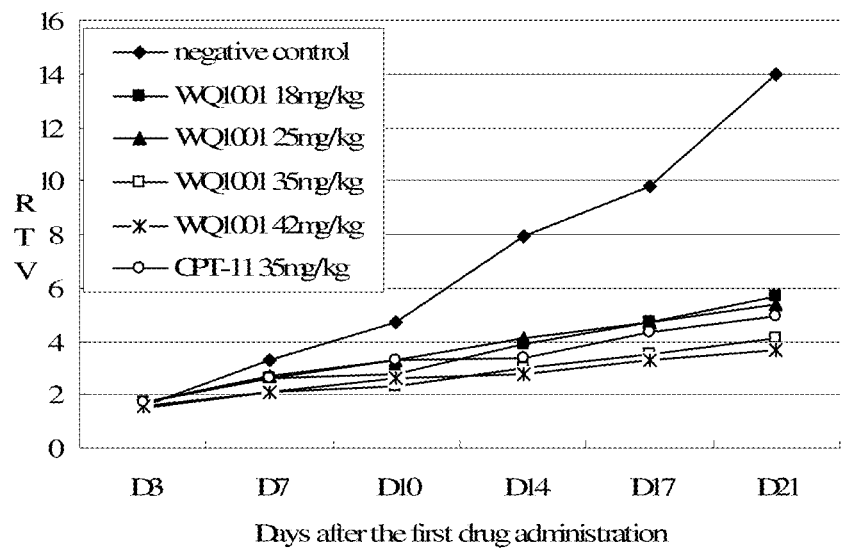
FIG. 15 shows relative change of tumor volumes in the in-vivo anti-tumor experiments of WQ1001 using the human colon cancer HT-29 nude mouse xenograft model.

Animal Study on Anticancer Evaluation Using the Human Colon Cancer HT-29 Nude Mouse Xenograft Model By the method of Example 10 and the drug administration scheme of Table 18, the anticancer activity of Compounds WQ1001 was measured using the human colon cancer HT-29 nude mouse xenograft model. The test results are detailed in FIG. 15 and Table 19. At the end of the test, tumor growth of all drug-treated groups was slower than that of the Negative Control Group. Administering the test drug WQ1001 18 mg/kg, 25 mg/kg and 35 mg/kg all significantly inhibited tumor growth, and the efficacy of 35 mg/kg was the best. It can also be concluded from the study that: under the condition of similar toxicity, the antitumor efficacy of WQ1001 is better than that of CPT-11.

TABLE 18

Drug administration scheme of the in vivo antitumor drug efficacy study of WQ1001 the human colon cancer HT-29 nude mouse xenograft model

| Group | | Animal count | Dosage (mg/kg) | Drug conc. (mg/ml) | Drug administration path & times | Volume of drug administration (ml/20 g) |
|---|---|---|---|---|---|---|
| Negative Control Group (NS) | | 10 | / | / | D0, 3, 7, 10, 14, 17 | 0.2 |
| Test Group (WQ1001) | Low Dosage Group | 8 | 18 | 1.8 | D0, 3, 7, 10, 14, 17 | 0.2 |
| | Medium Dosage Group | 8 | 25 | 2.5 | D0, 3, 7, 10, 14, 17 | 0.2 |
| | High Dosage Group | 8 | 35 | 3.5 | D0, 3, 7, 10, 14, 17 | 0.2 |
| Positive Control Group (CPT11) | | 8 | 35 | 3.5 | D0, 4, 7, 11, 14, 17 | 0.2 |

TABLE 19

Body-weight change and tumor inhibition effects of all groups in the WQ1001 in vivo antitumor efficacy test using the human colon cancer HT-29 nude mouse xenograft model

| Group | Drug administration schedule | Animal body-weight (g) Start | End | RTV22 | T22/C22 (%) |
|---|---|---|---|---|---|
| Negative Control Group | D0, 3, 7, 10, 14, 17 | 19.9 ± 0.5 | 19.3 ± 1.2 | 14.0 ± 3.0 | 100 |
| WQ1001 18 mg/kg | D0, 3, 7, 10, 14, 17 | 20.8 ± 1.0 | 18.2 ± 1.4 | 5.7 ± 1.2 | 41.0 |
| WQ1001 25 mg/kg | D0, 3, 7, 10, 14, 17 | 20.1 ± 0.6 | 18.4 ± 1.0 | 5.4 ± 1.3 | 38.9 |
| WQ1001 35 mg/kg | D0, 3, 7, 10, 14, 17 | 20.3 ± 0.9 | 18.1 ± 0.8 | 4.1 ± 1.8 | 29.5 |
| CPT-11 35 mg/kg | D0, 3, 7, 10, 14, 17 | 20.4 ± 1.2 | 18.7 ± 1.7 | 4.9 ± 1.3 | 35.0 |

EXAMPLE 12

Figure 16:
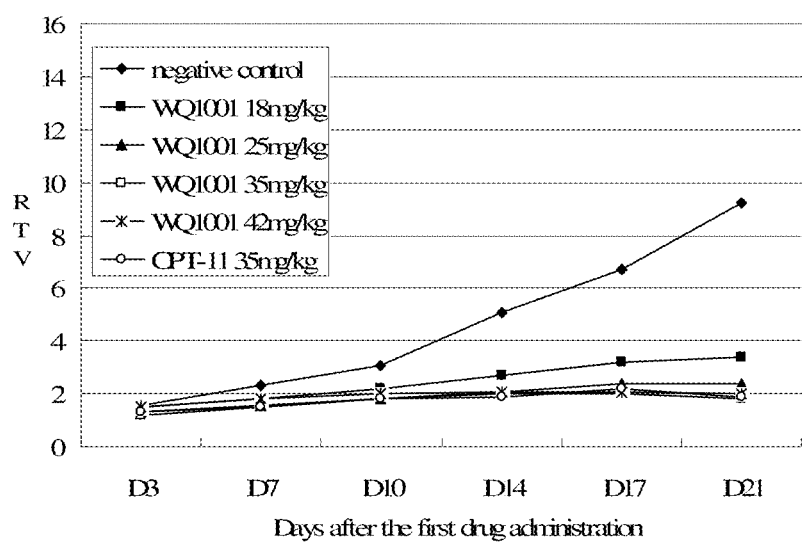
FIG. 16 shows relative change of tumor volumes in the in-vivo anti-tumor experiments of WQ1001 using the human breast cancer MCF-7 nude mouse xenograft model.

Animal Study on Anticancer Evaluation Using the Human Breast Cancer MCF-7 Nude Mouse Xenograft Model By the method of Example 10 and the drug administration scheme of Table 20, the anticancer activity of Compounds WQ1001 was measured using the human breast cancer MCF-7 nude mouse xenograft model. The test results are detailed in FIG. 16 and Table 21. At the end of the test, tumor growth of all drug-treated groups was slower than that of the Negative Control Group. Administering the test drug WQ1001 18 mg/kg, 25 mg/kg and 35 mg/kg all significantly inhibited tumor growth, and the efficacy of 35 mg/kg was the best. It can also be concluded from the study that: under the condition of similar toxicity, the antitumor efficacy of WQ1001 is better than that of CPT-11.

TABLE 20

Drug administration scheme of the in vivo antitumor drug efficacy study of WQ1001 the human breast cancer MCF-7 nude mouse xenograft model

| Group | | Animal count | Dosage (mg/kg) | Drug conc. (mg/ml) | Drug administration path & times | Volume of drug administration (ml/20 g) |
|---|---|---|---|---|---|---|
| Negative Control Group (NS) | | 10 | / | / | D0, 3, 7, 10, 14, 17 | 0.2 |
| Test Group (WQ1001) | Low Dosage Group | 8 | 18 | 1.8 | D0, 3, 7, 10, 14, 17 | 0.2 |
| | Medium Dosage Group | 8 | 25 | 2.5 | D0, 3, 7, 10, 14, 17 | 0.2 |
| | High Dosage Group | 8 | 35 | 3.5 | D0, 3, 7, 10, 14, 17 | 0.2 |
| Positive Control Group (CPT11) | | 8 | 35 | 3.5 | D0, 4, 7, 11, 14, 17 | 0.2 |

TABLE 21

Body-weight change and tumor inhibition effects of all groups in the WQ1001 in vivo antitumor efficacy test using the human breast cancer MCF-7 nude mouse xenograft model

| Group | Drug administration schedule | Animal body-weight (g) Start | Animal body-weight (g) End | RTV22 | T22/C22 (%) |
|---|---|---|---|---|---|
| Negative Control Group | D0, 3, 7, 10, 14, 17 | 19.1 ± 0.8 | 19.6 ± 1.1 | 9.2 ± 3.4 | 100 |
| WQ1001 18 mg/kg | D0, 3, 7, 10, 14, 17 | 18.8 ± 0.9 | 19.1 ± 1.7 | 3.4 ± 0.7 | 37.3 |
| WQ1001 25 mg/kg | D0, 3, 7, 10, 14, 17 | 19.0 ± 1.0 | 19.9 ± 0.8 | 2.4 ± 0.5 | 25.5 |
| WQ1001 35 mg/kg | D0, 3, 7, 10, 14, 17 | 18.9 ± 1.1 | 19.2 ± 1.4 | 1.8 ± 0.6 | 19.5 |
| CPT-11 35 mg/kg | D0, 3, 7, 10, 14, 17 | 19.0 ± 0.8 | 20.6 ± 1.4 | 1.9 ± 0.4 | 20.4 |

EXAMPLE 13

Animal Study on Anticancer Evaluation Using the Multiple Myeloma NCI-H929 Nude Mouse Xenograft Model By the method similar to that of Example 10 and the drug administration scheme of Table 22, the anticancer activity of Compounds WQ1001 was measured using the human multiple myeloma NCI-H929 nude mouse xenograft model. The human multiple myeloma NCI-H929 cells were grafted to nude mice. After 2 days, the mice were randomly divided into 5 groups by body weight: the Negative Control Group (saline), three groups for WQ1001 (Low Dosage Group, Medium Dosage Group, and High Dosage Group), and the Positive Control Group (topotecan). Two days after tumor cell implantation, the drugs were administered by intraperitoneal injection once every 4 days for a total of 3 injections (on Day 2, 6, 10 after cancer cell implantation). The body weight was measured every 2 days. Before each drug administration, and the drug amount was adjusted according to the body weight with injection volume of 0.2 ml per 20 mg body weight of the test mouse. At the end of the test (Day 11), the body weights were measured right before sacrificing the animals.

TABLE 22

Drug administration scheme of the in vivo antitumor drug efficacy study of WQ1001 the multiple myeloma NCI-H929 nude mouse xenograft model

| Group | | Animal count | Dosage (mg/kg) | Drug conc. (mg/ml) | Drug administration path & times | Volume of drug administration (ml/20 g) |
|---|---|---|---|---|---|---|
| Negative Control Group (NS) | | 8 | / | / | D2, 6, 10 | 0.2 |
| Test Group (WQ1001) | Low Dosage Group | 8 | 18 | 1.8 | D2, 6, 10 | 0.2 |
| | Medium Dosage Group | 8 | 25 | 2.5 | D2, 6, 10 | 0.2 |
| | High Dosage Group | 8 | 35 | 3.5 | D2, 6, 10 | 0.2 |
| Positive Control Group (topotecan) | | 8 | 2 | 0.2 | D2, 6, 10 | 0.2 |

Figure 17:
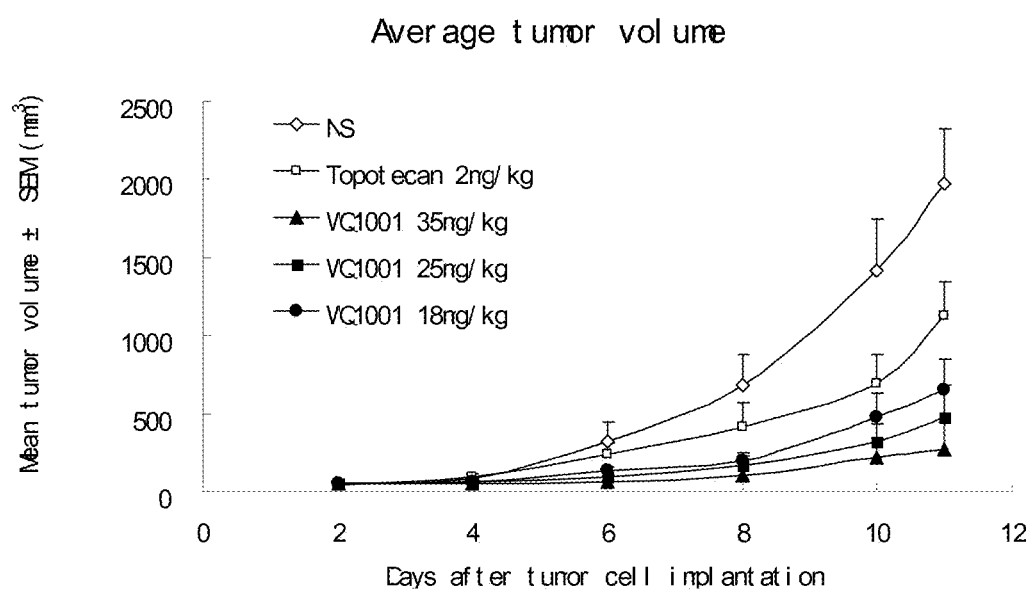
FIG. 17 shows relative change of tumor volumes in the in-vivo anti-tumor experiments of WQ1001 using the human multiple myeloma NCI-H929 nude mouse xenograft mode.

The drug was administrated right after the group division. The average body weight changes of all drug Groups during the test were similar, showing similar animal toxicity. At the end of the test, tumor growth of all drug-treated groups was slower than that of the Negative Control Group. Administering the test drug WQ1001 18 mg/kg, 25 mg/kg and 35 mg/kg all significantly inhibited tumor growth, and the efficacy of 35 mg/kg was the best. The antitumor efficacy of the test drug WQ1001 at all dosage levels was significantly better that of topotecan (positive control drug). It can also be concluded from the study of animal toxicity (animal body-weight change) and antitumor efficacy that under the condition of similar animal toxicity, antitumor efficacy of WQ1001 is much better than that of topotecan. The test results are detailed in Table 23 and FIG. 17.

TABLE 23

Body-weight change and tumor inhibition effects of all groups in the WQ1001 in vivo antitumor efficacy test

| Group | Drug administration schedule | Animal body-weight (g) Start | Animal body-weight (g) End | RTV11 | T11/C11 (%) |
|---|---|---|---|---|---|
| Negative Control Group | D2, 6, 10 | 17.4 ± 0.7 | 20.6 ± 1.4 | 40.3 ± 18.5 | 100 |
| WQ1001 10 mg/kg | D2, 6, 10 | 17.2 ± 1.0 | 19.2 ± 1.3 | 13.5 ± 11.0 | 13.9 |
| WQ1001 20 mg/kg | D2, 6, 10 | 17.3 ± 0.7 | 18.8 ± 0.6 | 9.80 ± 11.6 | 24.3 |
| WQ1001 40 mg/kg | D2, 6, 10 | 17.3 ± 0.7 | 18.5 ± 0.7 | 5.61 ± 9.74 | 33.5 |
| Topotecan 10 mg/kg | D2, 6, 10 | 21.0 ± 1.6 | 19.2 ± 0.9 | 25.3 ± 14.8 | 62.7 |

The foregoing description of the embodiments will so fully reveal the general nature of the invention that others can, by applying existing knowledge, readily modify and/or adapt for various applications such embodiments without departing from the scope of the present invention, and therefore such adaptations and modifications are intended to be comprehended as equivalents of the disclosed embodiments.

What is claimed is:

1. A compound or its pharmaceutically acceptable salts, comprising

A phosphite group; and a chemical selected from the group consisting of compounds listed in Table 1;

TABLE 1

| Compounds | Structural Formula |
|---|---|
| Camptothecin | |
| SN38 | |
| Topotecan | |
| 9-amino-CPT | |
| Irinotecan | |

TABLE 1-continued

| Compounds | Structural Formula |
|---|---|
| 9-nitro-CPT | |
| Lurtotecan | |
| 7-ethyl-10,11-methylenedioxy-CPT | |
| Exatecan | |
| 7-ethyl-CPT | |

TABLE 1-continued

| Compounds | Structural Formula |
|---|---|
| 10-Hydroxy-CPT (SN22) |  |
| Gimatecan | |
| Karenitecan | |
| Silatecan | | wherein the phosphite group is covalently attached to the C-20 site of the chemical.

2. The compound of claim 1, wherein the compound is a salt and the positive ion is $K^+$, $Na^+$, $Li^+$, $Mg^{2+}$, $Ca^{2+}$, $Zn^{2+}$, $Fe^{3+}$ or ammonium ion.

3. The compound of claim 2, wherein the ammonium is derived from one of following bases: $NH_3$, monomethylamine, dimethylamine, trimethylamine, monoethylamine, diethylamine, triethylamine, methylethylamine, dimethylethylamine, diisopropylamine, pyrrolidine, dihydro-isoindol, morpholine, N,N-diallyl amine, 4-methyl piperidine, ethanolamine, 5-bromo dihydro-isoindol, thiomorpholine, cis-2,6-dimethylmorpholine and ethylenediamine.

4. A method for preparing the compound of claim 1, including the following steps:

(1) reacting $PCl_3$ with an azole compound of RH, producing a phosphine triamine intermediate of Formula III:

Formula III $$R-P-R$$
$$|$$
$$R$$

wherein, R represents

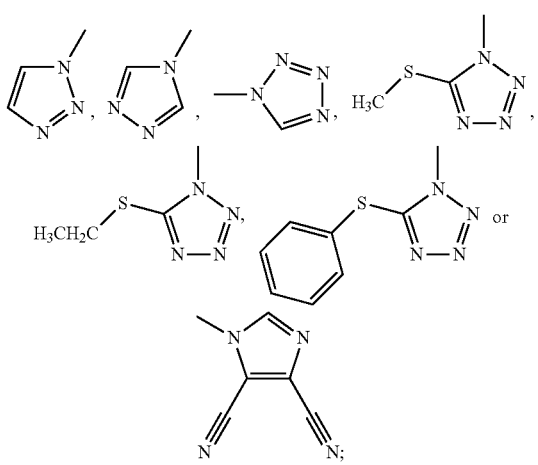

(2) reacting the phosphine triamine intermediate of Formula III with a compound of Formula IV, producing a CPT 20(S)—O-phosphoramidite precursor of Formula V:

Formula IV

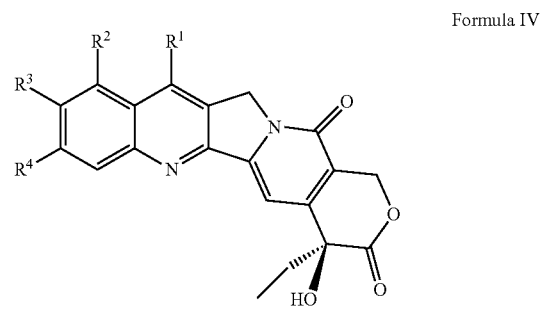

Formula V

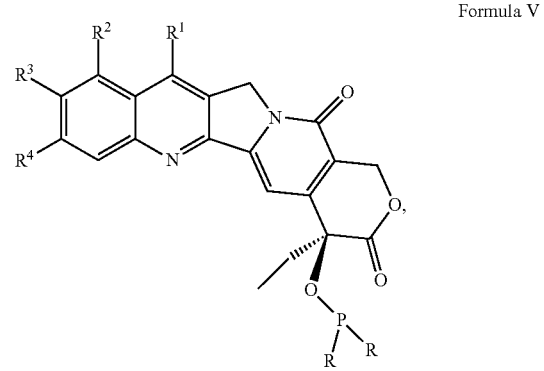

wherein $R^1$, $R^2$, $R^3$, and $R^4$ are the same as defined in claim 1, and when R¹, R², R³, or R⁴ is or contains a hydroxyl group or an amino group, wherein the hydroxyl group or the amino group is protected with a protecting group before reacting with the compound of Formula III;

(3) hydrolyzing the precursor of Formula V, producing the CPT 20(S)—O— phosphite of Formula I:

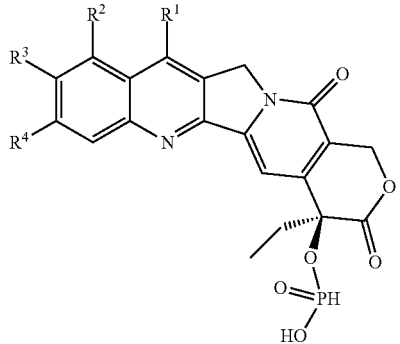

Formula I when R¹, R², R³, or R⁴ is or contains a protected amino or hydroxyl group, the protecting group is removed, (4) optionally, saltifying the compound of Formula I, producing the corresponding salts.

5. A pharmaceutical composition, comprising the camptothecin derivative of claim 1.

6. A method of treating a cancer, comprising Administrating to a subject an effective amount of the pharmaceutical composition according to claim 5 under conditions wherein the pharmaceutical composition inhibits, retards, and/or kills cancer cells in the subject; wherein said cancer is selected from the group consisting of lung cancer, breast cancer, colon cancer, rectal cancer, prostate cancer, melanoma, pancreas cancer, stomach cancer, liver cancer, brain cancer, kidney cancer, uterus cancer, cervix cancer, ovaries cancer, urinary tract cancer, gastrointestinal cancer, myeloma, and leukemia cancer.

7. The method of claim 6, wherein said cancer is breast cancer.

8. The method of claim 6, wherein said cancer is small cell lung cancer.

9. The method of claim 6, wherein said cancer is colon cancer.

10. The method of claim 6, wherein said cancer is rectal cancer.

11. The method of claim 6, wherein said cancer is multiple myeloma cancer.

12. A pharmaceutical composition, comprising the camptothecin derivative of Claim 2.

13. The pharmaceutical composition of claim 12, wherein the ammonium ion is derived from any of the following bases: NH₃, monomethylamine, dimethylamine, trimethylamine, monoethylamine, diethylamine, triethylamine, methylethylamine, dimethylethylamine, diisopropylamine, pyrrolidine, dihydro-isoindol, morpholine, N,N-diallyl amine, 4-methyl piperidine, ethanolamine, 5-bromo dihydro-isoindol, thiomorpholine, cis-2,6dimethylmorpholine and ethylenediamine.

14. A method of treating a cancer, comprising Administrating to a subject an effective amount of the pharmaceutical composition comprising the compound of claim 2 under conditions wherein the pharmaceutical composition inhibits, retards, and/or kills cancer cells in the subject;

wherein said cancer is selected from the group consisting of lung cancer, breast cancer, colon cancer, rectal cancer, prostate cancer, melanoma, pancreas cancer, stomach cancer, liver cancer, brain cancer, kidney cancer, uterus cancer, cervix cancer, ovaries cancer, urinary tract cancer, gastrointestinal cancer, myeloma, and leukemia cancer.

* * * * *

UNITED STATES PATENT AND TRADEMARK OFFICE
CERTIFICATE OF CORRECTION

Page 1 of 1

PATENT NO. : 9,266,911 B2
APPLICATION NO. : 14/134346
DATED : February 23, 2016
INVENTOR(S) : Wenqiang Zhou and Jing Deng It is certified that error appears in the above-identified patent and that said Letters Patent is hereby corrected as shown below:

In the Claims:

Col. 37, Claim 5, lines 28 and 29 should read
5. A pharmaceutical composition, comprising the compound of Claim 1.

Col. 38, Claim 12, lines 14 and 15 should read
12. A pharmaceutical composition, comprising the compound of Claim 2.

Signed and Sealed this
Tenth Day of May, 2016

Michelle K. Lee
*Director of the United States Patent and Trademark Office*